(12) United States Patent
Ma et al.

(10) Patent No.: US 7,608,587 B2
(45) Date of Patent: Oct. 27, 2009

(54) EXENDIN 4 POLYPEPTIDE FRAGMENT

(75) Inventors: Xiaopeng Ma, Jiangsu (CN); Bing Wang, Jiangsu (CN); Shaoqi Xi, Jiangsu (CN)

(73) Assignee: Changzhou Pharmaceutical Factory (CN)

( * ) Notice: Subject to any disclaimer, the term of this patent is extended or adjusted under 35 U.S.C. 154(b) by 180 days.

(21) Appl. No.: 11/497,075

(22) Filed: Aug. 1, 2006

(65) Prior Publication Data
US 2007/0037747 A1 Feb. 15, 2007

Related U.S. Application Data

(63) Continuation-in-part of application No. 11/357,614, filed on Feb. 17, 2006, now abandoned.

(30) Foreign Application Priority Data
Jun. 29, 2005 (CN) .......................... 2005 1 0040823

(51) Int. Cl.
*A61K 38/12* (2006.01)
(52) U.S. Cl. .............................. 514/12; 530/324; 514/3

(58) Field of Classification Search ........................ None
See application file for complete search history.

(56) References Cited

U.S. PATENT DOCUMENTS 5,424,286 A 6/1995 Eng ............................. 514/2
2007/0203058 A1* 8/2007 Lau et al. ...................... 514/12

FOREIGN PATENT DOCUMENTS

| EP | 1 386 930 A1 * | 2/2004 |
| WO | WO 2004/035754 A3 | 4/2004 |
| WO | WO 2004/036186 A | 4/2004 |

* cited by examiner

*Primary Examiner*—Andrew D Kosar
*Assistant Examiner*—Satyanarayana R Gudibande
(74) *Attorney, Agent, or Firm*—Thomas, Kayden, Horstemeyer & Risley, LLP

(57) ABSTRACT

The present invention relates to an Exendin 4 polypeptide fragment, which has hypoglycemic activity, and can be used for the treatment of type II diabetes mellitus. The polypeptide sequence described herein is HGEGTX$_1$TSDLSKQX$_2$EEEAVX$_3$LFIEWLKNGX$_4$PX$_5$, where X$_1$ represents Phe or Tyr, X$_2$ represents Met, Ile or Leu, X$_3$ represents Lys, X$_4$ represents Gly or deletion, X$_5$ represents Arg or deletion. Additionally, the present invention relates to a method for the Exendin 4 polypeptide fragment preparation.

10 Claims, 33 Drawing Sheets

SEQUENCE LISTING

<160> NUMBER OF SEQ ID NOS: 72

<210> SEQ ID NO 1
<211> LENGTH: 32
<212> TYPE: PRT
<213> ORGANISM: Artificial
<220> FEATURE:
<223> OTHER INFORMATION: Exendin 4 polypeptide fragment

<400> SEQUENCE: 1

His Gly Glu Gly Thr Phe Thr Ser Asn Leu Ser Lys Gln Met Glu Glu
1               5                   10                  15

Glu Ala Val Lys Leu Phe Ile Glu Trp Leu Lys Asn Gly Gly Pro Arg
            20                  25                  30

<210> SEQ ID NO 2
<211> LENGTH: 32
<212> TYPE: PRT
<213> ORGANISM: Artificial
<220> FEATURE:
<223> OTHER INFORMATION: Exendin 4 polypeptide fragment

<400> SEQUENCE: 2

His Gly Glu Gly Thr Tyr Thr Ser Asn Leu Ser Lys Gln Met Glu Glu
1               5                   10                  15

Glu Ala Val Lys Leu Phe Ile Glu Trp Leu Lys Asn Gly Gly Pro Arg
            20                  25                  30

<210> SEQ ID NO 3
<211> LENGTH: 31
<212> TYPE: PRT
<213> ORGANISM: Artificial
<220> FEATURE:
<223> OTHER INFORMATION: Exendin 4 polypeptide fragment

<400> SEQUENCE: 3

His Gly Glu Gly Thr Phe Thr Ser Asn Leu Ser Lys Gln Met Glu Glu
1               5                   10                  15

Glu Ala Val Lys Leu Phe Ile Glu Trp Leu Lys Asn Gly Pro Arg
            20                  25                  30

<210> SEQ ID NO 4
<211> LENGTH: 31
<212> TYPE: PRT
<213> ORGANISM: Artificial
<220> FEATURE:
<223> OTHER INFORMATION: Exendin 4 polypeptide fragment

<400> SEQUENCE: 4

His Gly Glu Gly Thr Tyr Thr Ser Asn Leu Ser Lys Gln Met Glu Glu
1               5                   10                  15

Glu Ala Val Lys Leu Phe Ile Glu Trp Leu Lys Asn Gly Pro Arg
            20                  25                  30

<210> SEQ ID NO 5
<211> LENGTH: 32
<212> TYPE: PRT
<213> ORGANISM: Artificial
<220> FEATURE:
<223> OTHER INFORMATION: Exendin 4 polypeptide fragment

<400> SEQUENCE: 5

His Gly Glu Gly Thr Phe Thr Ser Asn Leu Ser Lys Gln Ile Glu Glu

```
                1               5                  10                 15
Glu Ala Val Lys Leu Phe Ile Glu Trp Leu Lys Asn Gly Gly Pro Arg
            20                  25                 30

<210> SEQ ID NO 6
<211> LENGTH: 32
<212> TYPE: PRT
<213> ORGANISM: Artificial
<220> FEATURE:
<223> OTHER INFORMATION: Exendin 4 polypeptide fragment

<400> SEQUENCE: 6

His Gly Glu Gly Thr Tyr Thr Ser Asn Leu Ser Lys Gln Ile Glu Glu
1               5                   10                  15

Glu Ala Val Lys Leu Phe Ile Glu Trp Leu Lys Asn Gly Gly Pro Arg
            20                  25                  30

<210> SEQ ID NO 7
<211> LENGTH: 31
<212> TYPE: PRT
<213> ORGANISM: Artificial
<220> FEATURE:
<223> OTHER INFORMATION: Exendin 4 polypeptide fragment

<400> SEQUENCE: 7

His Gly Glu Gly Thr Phe Thr Ser Asn Leu Ser Lys Gln Ile Glu Glu
1               5                   10                  15

Glu Ala Val Lys Leu Phe Ile Glu Trp Leu Lys Asn Gly Pro Arg
            20                  25                  30

<210> SEQ ID NO 8
<211> LENGTH: 31
<212> TYPE: PRT
<213> ORGANISM: Artificial
<220> FEATURE:
<223> OTHER INFORMATION: Exendin 4 polypeptide fragment gene

<400> SEQUENCE: 8

His Gly Glu Gly Thr Tyr Thr Ser Asn Leu Ser Lys Gln Ile Glu Glu
1               5                   10                  15

Glu Ala Val Lys Leu Phe Ile Glu Trp Leu Lys Asn Gly Pro Arg
            20                  25                  30

<210> SEQ ID NO 9
<211> LENGTH: 32
<212> TYPE: PRT
<213> ORGANISM: Artificial
<220> FEATURE:
<223> OTHER INFORMATION: Exendin 4 polypeptide fragment

<400> SEQUENCE: 9

His Gly Glu Gly Thr Phe Thr Ser Asn Leu Ser Lys Gln Leu Glu Glu
1               5                   10                  15

Glu Ala Val Lys Leu Phe Ile Glu Trp Leu Lys Asn Gly Gly Pro Arg
            20                  25                  30

<210> SEQ ID NO 10
<211> LENGTH: 32
<212> TYPE: PRT
<213> ORGANISM: Artificial
<220> FEATURE:
<223> OTHER INFORMATION: Exendin 4 polypeptide fragment

<400> SEQUENCE: 10
```

His Gly Glu Gly Thr Tyr Thr Ser Asn Leu Ser Lys Gln Leu Glu Glu
1               5                   10                  15

Glu Ala Val Lys Leu Phe Ile Glu Trp Leu Lys Asn Gly Gly Pro Arg
            20                  25                  30

```
<210> SEQ ID NO 11
<211> LENGTH: 31
<212> TYPE: PRT
<213> ORGANISM: Artificial
<220> FEATURE:
<223> OTHER INFORMATION: Exendin 4 polypeptide fragment

<400> SEQUENCE: 11
```

His Gly Glu Gly Thr Phe Thr Ser Asn Leu Ser Lys Gln Leu Glu Glu
1               5                   10                  15

Glu Ala Val Lys Leu Phe Ile Glu Trp Leu Lys Asn Gly Pro Arg
            20                  25                  30

```
<210> SEQ ID NO 12
<211> LENGTH: 31
<212> TYPE: PRT
<213> ORGANISM: Artificial
<220> FEATURE:
<223> OTHER INFORMATION: Exendin 4 polypeptide fragment

<400> SEQUENCE: 12
```

His Gly Glu Gly Thr Tyr Thr Ser Asn Leu Ser Lys Gln Leu Glu Glu
1               5                   10                  15

Glu Ala Val Lys Leu Phe Ile Glu Trp Leu Lys Asn Gly Pro Arg
            20                  25                  30

```
<210> SEQ ID NO 13
<211> LENGTH: 57
<212> TYPE: DNA
<213> ORGANISM: Artificial
<220> FEATURE:
<223> OTHER INFORMATION: Exendin 4 polypeptide fragment gene

<400> SEQUENCE: 13
```
aattccagat ctatgcgtca cggcgaaggc accttcacca gcgatctgag caaacag      57

```
<210> SEQ ID NO 14
<211> LENGTH: 66
<212> TYPE: DNA
<213> ORGANISM: Artificial
<220> FEATURE:
<223> OTHER INFORMATION: Exendin 4 polypeptide fragment gene

<400> SEQUENCE: 14
```
atggaagaag aagcggttaa actgttcatc gaatggctga aaaacggcgg cccgcgtgga      60
tcctag                                                                66

```
<210> SEQ ID NO 15
<211> LENGTH: 65
<212> TYPE: DNA
<213> ORGANISM: Artificial
<220> FEATURE:
<223> OTHER INFORMATION: Exendin 4 polypeptide fragment gene

<400> SEQUENCE: 15
```
tcgactagga tccacgcggg ccgccgtttt tcagccattc gatgaacagt ttaaccgctt      60
cttct                                                                 65

<210> SEQ ID NO 16
<211> LENGTH: 58
<212> TYPE: DNA
<213> ORGANISM: Artificial
<220> FEATURE:
<223> OTHER INFORMATION: Exendin 4 polypeptide fragment gene

<400> SEQUENCE: 16
tccatctgtt tgctcagatc gctggtgaag gtgccttcgc cgtgacgcat agatctgg      58

<210> SEQ ID NO 17
<211> LENGTH: 57
<212> TYPE: DNA
<213> ORGANISM: Artificial
<220> FEATURE:
<223> OTHER INFORMATION: Exendin 4 polypeptide fragment gene

<400> SEQUENCE: 17
aattccagat ctatgcgtca cggcgaaggc acctacacca gcgatctgag caaacag       57

<210> SEQ ID NO 18
<211> LENGTH: 66
<212> TYPE: DNA
<213> ORGANISM: Artificial
<220> FEATURE:
<223> OTHER INFORMATION: Exendin 4 polypeptide fragment gene

<400> SEQUENCE: 18
atggaagaag aagcggttaa actgttcatc gaatggctga aaaacggcgg cccgcgtgga    60
tcctag                                                               66

<210> SEQ ID NO 19
<211> LENGTH: 65
<212> TYPE: DNA
<213> ORGANISM: Artificial
<220> FEATURE:
<223> OTHER INFORMATION: Exendin 4 polypeptide fragment gene

<400> SEQUENCE: 19
tcgactagga tccacgcggg ccgccgtttt cagccattc gatgaacagt ttaaccgctt     60
cttct                                                                65

<210> SEQ ID NO 20
<211> LENGTH: 58
<212> TYPE: DNA
<213> ORGANISM: Artificial
<220> FEATURE:
<223> OTHER INFORMATION: Exendin 4 polypeptide fragment gene

<400> SEQUENCE: 20
tccatctgtt tgctcagatc gctggtgtag gtgccttcgc cgtgacgcat agatctgg      58

<210> SEQ ID NO 21
<211> LENGTH: 57
<212> TYPE: DNA
<213> ORGANISM: Artificial
<220> FEATURE:
<223> OTHER INFORMATION: Exendin 4 polypeptide fragment gene

<400> SEQUENCE: 21
aattccagat ctatgcgtca cggcgaaggc accttcacca gcgatctgag caaacag       57

<210> SEQ ID NO 22
<211> LENGTH: 63
<212> TYPE: DNA

```
<213> ORGANISM: Artificial
<220> FEATURE:
<223> OTHER INFORMATION: Exendin 4 polypeptide fragment gene

<400> SEQUENCE: 22
atggaagaag aagcggttaa actgttcatc gaatggctga aaaacggccc gcgtggatcc      60
tag                                                                   63

<210> SEQ ID NO 23
<211> LENGTH: 62
<212> TYPE: DNA
<213> ORGANISM: Artificial
<220> FEATURE:
<223> OTHER INFORMATION: Exendin 4 polypeptide fragment gene

<400> SEQUENCE: 23
tcgactagga tccacgcggg ccgttttttca gccattcgat gaacagttta accgcttctt    60
ct                                                                    62

<210> SEQ ID NO 24
<211> LENGTH: 58
<212> TYPE: DNA
<213> ORGANISM: Artificial
<220> FEATURE:
<223> OTHER INFORMATION: Exendin 4 polypeptide fragment gene

<400> SEQUENCE: 24
tccatctgtt tgctcagatc gctggtgaag gtgccttcgc cgtgacgcat agatctgg       58

<210> SEQ ID NO 25
<211> LENGTH: 57
<212> TYPE: DNA
<213> ORGANISM: Artificial
<220> FEATURE:
<223> OTHER INFORMATION: Exendin 4 polypeptide fragment gene

<400> SEQUENCE: 25
aattccagat ctatgcgtca cggcgaaggc acctacacca gcgatctgag caaacag        57

<210> SEQ ID NO 26
<211> LENGTH: 63
<212> TYPE: DNA
<213> ORGANISM: Artificial
<220> FEATURE:
<223> OTHER INFORMATION: Exendin 4 polypeptide fragment gene

<400> SEQUENCE: 26
atggaagaag aagcggttaa actgttcatc gaatggctga aaaacggccc gcgtggatcc      60
tag                                                                   63

<210> SEQ ID NO 27
<211> LENGTH: 62
<212> TYPE: DNA
<213> ORGANISM: Artificial
<220> FEATURE:
<223> OTHER INFORMATION: Exendin 4 polypeptide fragment gene

<400> SEQUENCE: 27
tcgactagga tccacgcggg ccgttttttca gccattcgat gaacagttta accgcttctt    60
ct                                                                    62

<210> SEQ ID NO 28
<211> LENGTH: 58
```

```
<212> TYPE: DNA
<213> ORGANISM: Artificial
<220> FEATURE:
<223> OTHER INFORMATION: Exendin 4 polypeptide fragment gene

<400> SEQUENCE: 28
tccatctgtt tgctcagatc gctggtgtag gtgccttcgc cgtgacgcat agatctgg        58

<210> SEQ ID NO 29
<211> LENGTH: 57
<212> TYPE: DNA
<213> ORGANISM: Artificial
<220> FEATURE:
<223> OTHER INFORMATION: Exendin 4 polypeptide fragment gene

<400> SEQUENCE: 29
aattccagat ctatgcgtca cggcgaaggc accttcacca gcgatctgag caaacag         57

<210> SEQ ID NO 30
<211> LENGTH: 66
<212> TYPE: DNA
<213> ORGANISM: Artificial
<220> FEATURE:
<223> OTHER INFORMATION: Exendin 4 polypeptide fragment gene

<400> SEQUENCE: 30
atcgaagaag aagcggttaa actgttcatc gaatggctga aaaacggcgg cccgcgtgga      60
tcctag                                                                66

<210> SEQ ID NO 31
<211> LENGTH: 65
<212> TYPE: DNA
<213> ORGANISM: Artificial
<220> FEATURE:
<223> OTHER INFORMATION: Exendin 4 polypeptide fragment gene

<400> SEQUENCE: 31
tcgactagga tccacgcggg ccgccgtttt tcagccattc gatgaacagt ttaaccgctt      60
cttct                                                                 65

<210> SEQ ID NO 32
<211> LENGTH: 58
<212> TYPE: DNA
<213> ORGANISM: Artificial
<220> FEATURE:
<223> OTHER INFORMATION: Exendin 4 polypeptide fragment gene

<400> SEQUENCE: 32
tcgatctgtt tgctcagatc gctggtgaag gtgccttcgc cgtgacgcat agatctgg        58

<210> SEQ ID NO 33
<211> LENGTH: 57
<212> TYPE: DNA
<213> ORGANISM: Artificial
<220> FEATURE:
<223> OTHER INFORMATION: Exendin 4 polypeptide fragment gene

<400> SEQUENCE: 33
aattccagat ctatgcgtca cggcgaaggc acctacacca gcgatctgag caaacag         57

<210> SEQ ID NO 34
<211> LENGTH: 66
<212> TYPE: DNA
<213> ORGANISM: Artificial
<220> FEATURE:
```

<223> OTHER INFORMATION: Exendin 4 polypeptide fragment gene

<400> SEQUENCE: 34
atcgaagaag aagcggttaa actgttcatc gaatggctga aaacggcgg cccgcgtgga    60 tcctag                                                              66

<210> SEQ ID NO 35
<211> LENGTH: 65
<212> TYPE: DNA
<213> ORGANISM: Artificial
<220> FEATURE:
<223> OTHER INFORMATION: Exendin 4 polypeptide fragment gene

<400> SEQUENCE: 35
tcgactagga tccacgcggg ccgccgtttt tcagccattc gatgaacagt ttaaccgctt    60
cttct                                                               65

<210> SEQ ID NO 36
<211> LENGTH: 58
<212> TYPE: DNA
<213> ORGANISM: Artificial
<220> FEATURE:
<223> OTHER INFORMATION: Exendin 4 polypeptide fragment gene

<400> SEQUENCE: 36
tcgatctgtt tgctcagatc gctggtgtag gtgccttcgc cgtgacgcat agatctgg      58

<210> SEQ ID NO 37
<211> LENGTH: 57
<212> TYPE: DNA
<213> ORGANISM: Artificial
<220> FEATURE:
<223> OTHER INFORMATION: Exendin 4 polypeptide fragment gene

<400> SEQUENCE: 37
aattccagat ctatgcgtca cggcgaaggc accttcacca gcgatctgag caaacag       57

<210> SEQ ID NO 38
<211> LENGTH: 63
<212> TYPE: DNA
<213> ORGANISM: Artificial
<220> FEATURE:
<223> OTHER INFORMATION: Exendin 4 polypeptide fragment gene

<400> SEQUENCE: 38
atcgaagaag aagcggttaa actgttcatc gaatggctga aaacggccc gcgtggatcc    60 tag                                                                 63

<210> SEQ ID NO 39
<211> LENGTH: 62
<212> TYPE: DNA
<213> ORGANISM: Artificial
<220> FEATURE:
<223> OTHER INFORMATION: Exendin 4 polypeptide fragment gene

<400> SEQUENCE: 39
tcgactagga tccacgcggg ccgttttca gccattcgat gaacagttta accgcttctt    60
ct                                                                  62

<210> SEQ ID NO 40
<211> LENGTH: 58
<212> TYPE: DNA
<213> ORGANISM: Artificial

```
<220> FEATURE:
<223> OTHER INFORMATION: Exendin 4 polypeptide fragment gene

<400> SEQUENCE: 40
tcgatctgtt tgctcagatc gctggtgaag gtgccttcgc cgtgacgcat agatctgg      58

<210> SEQ ID NO 41
<211> LENGTH: 57
<212> TYPE: DNA
<213> ORGANISM: Artificial
<220> FEATURE:
<223> OTHER INFORMATION: Exendin 4 polypeptide fragment gene

<400> SEQUENCE: 41
aattccagat ctatgcgtca cggcgaaggc acctacacca gcgatctgag caaacag       57

<210> SEQ ID NO 42
<211> LENGTH: 63
<212> TYPE: DNA
<213> ORGANISM: Artificial
<220> FEATURE:
<223> OTHER INFORMATION: Exendin 4 polypeptide fragment gene

<400> SEQUENCE: 42
atcgaagaag aagcggttaa actgttcatc gaatggctga aaaacggccc cgtggatcc     60 tag                                                                  63

<210> SEQ ID NO 43
<211> LENGTH: 62
<212> TYPE: DNA
<213> ORGANISM: Artificial
<220> FEATURE:
<223> OTHER INFORMATION: Exendin 4 polypeptide fragment gene

<400> SEQUENCE: 43
tcgactagga tccacgcggg ccgttttttca gccattcgat gaacagttta accgcttctt   60
ct                                                                   62

<210> SEQ ID NO 44
<211> LENGTH: 58
<212> TYPE: DNA
<213> ORGANISM: Artificial
<220> FEATURE:
<223> OTHER INFORMATION: Exendin 4 polypeptide fragment gene

<400> SEQUENCE: 44
tcgatctgtt tgctcagatc gctggtgtag gtgccttcgc cgtgacgcat agatctgg      58

<210> SEQ ID NO 45
<211> LENGTH: 57
<212> TYPE: DNA
<213> ORGANISM: Artificial
<220> FEATURE:
<223> OTHER INFORMATION: Exendin 4 polypeptide fragment gene

<400> SEQUENCE: 45
aattccagat ctatgcgtca cggcgaaggc accttcacca gcgatctgag caaacag       57

<210> SEQ ID NO 46
<211> LENGTH: 66
<212> TYPE: DNA
<213> ORGANISM: Artificial
<220> FEATURE:
<223> OTHER INFORMATION: Exendin 4 polypeptide fragment gene
```

```
<400> SEQUENCE: 46
ctggaagaag aagcggttaa actgttcatc gaatggctga aaaacggcgg cccgcgtgga    60
tcctag                                                                66

<210> SEQ ID NO 47
<211> LENGTH: 65
<212> TYPE: DNA
<213> ORGANISM: Artificial
<220> FEATURE:
<223> OTHER INFORMATION: Exendin 4 polypeptide fragment gene

<400> SEQUENCE: 47
tcgactagga tccacgcggg ccgccgtttt tcagccattc gatgaacagt ttaaccgctt    60
cttct                                                                 65

<210> SEQ ID NO 48
<211> LENGTH: 58
<212> TYPE: DNA
<213> ORGANISM: Artificial
<220> FEATURE:
<223> OTHER INFORMATION: Exendin 4 polypeptide fragment gene

<400> SEQUENCE: 48
tccagctgtt tgctcagatc gctggtgaag gtgccttcgc cgtgacgcat agatctgg      58

<210> SEQ ID NO 49
<211> LENGTH: 57
<212> TYPE: DNA
<213> ORGANISM: Artificial
<220> FEATURE:
<223> OTHER INFORMATION: Exendin 4 polypeptide fragment gene

<400> SEQUENCE: 49
aattccagat ctatgcgtca cggcgaaggc acctacacca gcgatctgag caaacag       57

<210> SEQ ID NO 50
<211> LENGTH: 66
<212> TYPE: DNA
<213> ORGANISM: Artificial
<220> FEATURE:
<223> OTHER INFORMATION: Exendin 4 polypeptide fragment gene

<400> SEQUENCE: 50
ctggaagaag aagcggttaa actgttcatc gaatggctga aaaacggcgg cccgcgtgga    60
tcctag                                                                66

<210> SEQ ID NO 51
<211> LENGTH: 65
<212> TYPE: DNA
<213> ORGANISM: Artificial
<220> FEATURE:
<223> OTHER INFORMATION: Exendin 4 polypeptide fragment gene

<400> SEQUENCE: 51
tcgactagga tccacgcggg ccgccgtttt tcagccattc gatgaacagt ttaaccgctt    60
cttct                                                                 65

<210> SEQ ID NO 52
<211> LENGTH: 58
<212> TYPE: DNA
<213> ORGANISM: Artificial
<220> FEATURE:
<223> OTHER INFORMATION: Exendin 4 polypeptide fragment gene
```

```
<400> SEQUENCE: 52
tccagctgtt tgctcagatc gctggtgtag gtgccttcgc cgtgacgcat agatctgg        58

<210> SEQ ID NO 53
<211> LENGTH: 57
<212> TYPE: DNA
<213> ORGANISM: Artificial
<220> FEATURE:
<223> OTHER INFORMATION: Exendin 4 polypeptide fragment gene

<400> SEQUENCE: 53
aattccagat ctatgcgtca cggcgaaggc accttcacca gcgatctgag caaacag        57

<210> SEQ ID NO 54
<211> LENGTH: 63
<212> TYPE: DNA
<213> ORGANISM: Artificial
<220> FEATURE:
<223> OTHER INFORMATION: Exendin 4 polypeptide fragment gene

<400> SEQUENCE: 54
ctggaagaag aagcggttaa actgttcatc gaatggctga aaaacggccc gcgtggatcc        60
tag                                                                    63

<210> SEQ ID NO 55
<211> LENGTH: 62
<212> TYPE: DNA
<213> ORGANISM: Artificial
<220> FEATURE:
<223> OTHER INFORMATION: Exendin 4 polypeptide fragment gene

<400> SEQUENCE: 55
tcgactagga tccacgcggg ccgttttcc gccattcgat gaacagttta accgcttctt        60
ct                                                                     62

<210> SEQ ID NO 56
<211> LENGTH: 58
<212> TYPE: DNA
<213> ORGANISM: Artificial
<220> FEATURE:
<223> OTHER INFORMATION: Exendin 4 polypeptide fragment gene

<400> SEQUENCE: 56
tccagctgtt tgctcagatc gctggtgaag gtgccttcgc cgtgacgcat agatctgg        58

<210> SEQ ID NO 57
<211> LENGTH: 57
<212> TYPE: DNA
<213> ORGANISM: Artificial
<220> FEATURE:
<223> OTHER INFORMATION: Exendin 4 polypeptide fragment gene

<400> SEQUENCE: 57
aattccagat ctatgcgtca cggcgaaggc acctacacca gcgatctgag caaacag        57

<210> SEQ ID NO 58
<211> LENGTH: 63
<212> TYPE: DNA
<213> ORGANISM: Artificial
<220> FEATURE:
<223> OTHER INFORMATION: Exendin 4 polypeptide fragment gene

<400> SEQUENCE: 58
```
ctggaagaag aagcggttaa actgttcatc gaatggctga aaaacggccc gcgtggatcc    60
tag                                                                  63

```
<210> SEQ ID NO 59
<211> LENGTH: 62
<212> TYPE: DNA
<213> ORGANISM: Artificial
<220> FEATURE:
<223> OTHER INFORMATION: Exendin 4 polypeptide fragment gene

<400> SEQUENCE: 59
```
tcgactagga tccacgcggg ccgttttttca gccattcgat gaacagttta accgcttctt    60
ct                                                                   62

```
<210> SEQ ID NO 60
<211> LENGTH: 58
<212> TYPE: DNA
<213> ORGANISM: Artificial
<220> FEATURE:
<223> OTHER INFORMATION: Exendin 4 polypeptide fragment gene

<400> SEQUENCE: 60
```
tccagctgtt tgctcagatc gctggtgtag gtgccttcgc cgtgacgcat agatctgg       58

```
<210> SEQ ID NO 61
<211> LENGTH: 31
<212> TYPE: PRT
<213> ORGANISM: Artificial
<220> FEATURE:
<223> OTHER INFORMATION: Exendin 4 polypeptide fragment

<400> SEQUENCE: 61
```

His Gly Glu Gly Thr Phe Thr Ser Asn Leu Ser Lys Gln Met Glu Glu
1               5                  10                  15

Glu Ala Val Lys Leu Phe Ile Glu Trp Leu Lys Asn Gly Gly Pro
            20                  25                  30

```
<210> SEQ ID NO 62
<211> LENGTH: 31
<212> TYPE: PRT
<213> ORGANISM: Artificial
<220> FEATURE:
<223> OTHER INFORMATION: Exendin 4 polypeptide fragment

<400> SEQUENCE: 62
```

His Gly Glu Gly Thr Tyr Thr Ser Asn Leu Ser Lys Gln Met Glu Glu
1               5                  10                  15

Glu Ala Val Lys Leu Phe Ile Glu Trp Leu Lys Asn Gly Gly Pro
            20                  25                  30

```
<210> SEQ ID NO 63
<211> LENGTH: 30
<212> TYPE: PRT
<213> ORGANISM: Artificial
<220> FEATURE:
<223> OTHER INFORMATION: Exendin 4 polypeptide fragment

<400> SEQUENCE: 63
```

His Gly Glu Gly Thr Phe Thr Ser Asn Leu Ser Lys Gln Met Glu Glu
1               5                  10                  15

Glu Ala Val Lys Leu Phe Ile Glu Trp Leu Lys Asn Gly Pro
            20                  25                  30

<210> SEQ ID NO 64
<211> LENGTH: 30
<212> TYPE: PRT
<213> ORGANISM: Artificial
<220> FEATURE:
<223> OTHER INFORMATION: Exendin 4 polypeptide fragment

<400> SEQUENCE: 64

His Gly Glu Gly Thr Tyr Thr Ser Asn Leu Ser Lys Gln Met Glu Glu
1               5                   10                  15

Glu Ala Val Lys Leu Phe Ile Glu Trp Leu Lys Asn Gly Pro
            20                  25                  30

<210> SEQ ID NO 65
<211> LENGTH: 31
<212> TYPE: PRT
<213> ORGANISM: Artificial
<220> FEATURE:
<223> OTHER INFORMATION: Exendin 4 polypeptide fragment

<400> SEQUENCE: 65

His Gly Glu Gly Thr Phe Thr Ser Asn Leu Ser Lys Gln Ile Glu Glu
1               5                   10                  15

Glu Ala Val Lys Leu Phe Ile Glu Trp Leu Lys Asn Gly Gly Pro
            20                  25                  30

<210> SEQ ID NO 66
<211> LENGTH: 31
<212> TYPE: PRT
<213> ORGANISM: Artificial
<220> FEATURE:
<223> OTHER INFORMATION: Exendin 4 polypeptide fragment

<400> SEQUENCE: 66

His Gly Glu Gly Thr Tyr Thr Ser Asn Leu Ser Lys Gln Ile Glu Glu
1               5                   10                  15

Glu Ala Val Lys Leu Phe Ile Glu Trp Leu Lys Asn Gly Gly Pro
            20                  25                  30

<210> SEQ ID NO 67
<211> LENGTH: 30
<212> TYPE: PRT
<213> ORGANISM: Artificial
<220> FEATURE:
<223> OTHER INFORMATION: Exendin 4 polypeptide fragment

<400> SEQUENCE: 67

His Gly Glu Gly Thr Phe Thr Ser Asn Leu Ser Lys Gln Ile Glu Glu
1               5                   10                  15

Glu Ala Val Lys Leu Phe Ile Glu Trp Leu Lys Asn Gly Pro
            20                  25                  30

<210> SEQ ID NO 68
<211> LENGTH: 30
<212> TYPE: PRT
<213> ORGANISM: Artificial
<220> FEATURE:
<223> OTHER INFORMATION: Exendin 4 polypeptide fragment

<400> SEQUENCE: 68

His Gly Glu Gly Thr Tyr Thr Ser Asn Leu Ser Lys Gln Ile Glu Glu
1               5                   10                  15

Glu Ala Val Lys Leu Phe Ile Glu Trp Leu Lys Asn Gly Pro
            20                  25                  30

```
<210> SEQ ID NO 69
<211> LENGTH: 31
<212> TYPE: PRT
<213> ORGANISM: Artificial
<220> FEATURE:
<223> OTHER INFORMATION: Exendin 4 polypeptide fragment

<400> SEQUENCE: 69

His Gly Glu Gly Thr Phe Thr Ser Asn Leu Ser Lys Gln Leu Glu Glu
1               5                   10                  15

Glu Ala Val Lys Leu Phe Ile Glu Trp Leu Lys Asn Gly Gly Pro
            20                  25                  30

<210> SEQ ID NO 70
<211> LENGTH: 31
<212> TYPE: PRT
<213> ORGANISM: Artificial
<220> FEATURE:
<223> OTHER INFORMATION: Exendin 4 polypeptide fragment

<400> SEQUENCE: 70

His Gly Glu Gly Thr Tyr Thr Ser Asn Leu Ser Lys Gln Leu Glu Glu
1               5                   10                  15

Glu Ala Val Lys Leu Phe Ile Glu Trp Leu Lys Asn Gly Gly Pro
            20                  25                  30

<210> SEQ ID NO 71
<211> LENGTH: 30
<212> TYPE: PRT
<213> ORGANISM: Artificial
<220> FEATURE:
<223> OTHER INFORMATION: Exendin 4 polypeptide fragment

<400> SEQUENCE: 71

His Gly Glu Gly Thr Phe Thr Ser Asn Leu Ser Lys Gln Leu Glu Glu
1               5                   10                  15

Glu Ala Val Lys Leu Phe Ile Glu Trp Leu Lys Asn Gly Pro
            20                  25                  30

<210> SEQ ID NO 72
<211> LENGTH: 30
<212> TYPE: PRT
<213> ORGANISM: Artificial
<220> FEATURE:
<223> OTHER INFORMATION: Exendin 4 polypeptide fragment

<400> SEQUENCE: 72

His Gly Glu Gly Thr Tyr Thr Ser Asn Leu Ser Lys Gln Leu Glu Glu
1               5                   10                  15

Glu Ala Val Lys Leu Phe Ile Glu Trp Leu Lys Asn Gly Pro
            20                  25                  30
```

EXENDIN 4 POLYPEPTIDE FRAGMENT

CROSS-REFERENCE TO RELATED APPLICATION

This application is a continuation-in-part of U.S. utility application entitled, "Exendin 4 Polypeptide Fragment," having Ser. No. 11/357,614, filed Feb. 17, 2006 now abandoned, which claims priority to Chinese Priority No. 2005/10040823.8 entitled "Exendin 4 polypeptide fragment", filed Jun. 29, 2005, both of which are entirely incorporated herein by reference.

FIELD OF THE INVENTION

The present invention relates to a truncated Exendin 4 polypeptide fragment, which has hypoglycemic activity, and can be used for the treatment of type II diabetes mellitus.

BACKGROUND ART

Due to the modern diet structure and life style, the population of diabetic patients increases year by year in many countries worldwide. Nowadays, there are 50 million patients in China, 60 million in India, 18 million in the USA and 6 million in Japan, respectively.

There are two main types of diabetes: insulin dependent diabetes (type I diabetes) and non-insulin dependent diabetes (type II diabetes). The cases with type II diabetes account for more than 90 percent of those with the disease. Patients with type II diabetes have various symptoms, such as postprandial insufficient insulin secretion, time delay of insulin secretion, high blood sugar levels and many others. The peripheral insulin acceptor in obese type II diabetic patients shows a decrease in the insulin sensitivity, thus resulting in elevated blood sugar levels with a high insulin level in the blood and a high hemoglobin (HbA1c) level of more than 8% (the non-diabetic range is 4-6%). As a result, the diabetic complications, such as heart disease and kidney failure, etc. occur. So the key to effectively treating type-II diabetes is to decrease the blood sugar level.

Nowadays, drugs used to treat diabetes fall into six broad categories: including the insulin secretagogues, such as sulfonylureas and Meglitinides; and the insulin non-secretagogues, such as insulin, alpha-glucosidase inhibitors, biguanides and Thiazolinediones. However, as shown in one tracking research report on thousands of type II diabetic patients by the UK Prospective Diabetes Study (UKPDS) for six years, none of the six classes of drugs mentioned above are effective on type II diabetic patients. They have all failed to prevent pancreas beta cells from incessant deterioration and have failed to decrease the HbAlc level, prevent diabetic complications, such as heart disease and kidney failure. Therefore, it is necessary to develop novel drugs for type II diabetes therapy.

In 1995, U.S. Pat. No. (5,424,286) for Exendin 4 was issued. Exendin 4 was isolated from the saliva of the Gila monster (Helode Suspectum) that lives in southwestern United States. This 39-amino-acid polypeptide shares 40% identity to glucagon-like peptide 1 (GLP-1) at the amino acid sequence level.

It was reported that Exendin 4, an analogue of GLP-1, binds to the GLP-1 receptor. Exendin 4 stimulates the proinsulin synthesis and insulin secretion, therefore decreasing the blood sugar level. Exendin 4 continues to act until blood sugar returns to normal level. Exendin 4 is safe and effective because it avoids stupor and shock due to hypoglycemia. The Exendin 4 decreases the HbA1c level, increases the beta cell amount, enhances the sensitivity of insulin receptors in the patients with type II diabetes, and inhibits the secretion of glucagons, etc. The commercially available Exendin 4 called Byetta was approved for the market by FDA in April 2005. (Refer to: Diabetes (1997) 46 433-439; ibid (1995) 44 1249-1258; Ibid (2002) 51 2796-2803; Ibid (1994) 53 2397-2403; Diabetes Care (2002) 25 330-336; Ibid (2000) 23 64-69; ibid (2004) 2 2623-2635; JAMA (2002) 287 373-379; N. Engl. J. Med. (2002) 346 393-436; Lanced (1998) 352 837-853; Diabetes Endocrinology (2005) 146 (4) 2069-2070; J. Clin. Endocrinology Metab (2004) 89 3469-3473.)

Efforts have been made to modify the Exendin 4 polypeptide by many researchers, aiming at obtaining more variants that are more effective and convenient to prepare and that provide more alternatives of Exendin 4. A truncated Exendin 4 polypeptide was announced in CN1227567A, which is comprised of 30 amino acid residues with Arg or Tyr at C-terminus. The Lilly Company in USA developed a series of GLP-1 analogues, capable of treating diabetes safely for the long term (Refer to WO02047716A). However, these examples mentioned above are quite limited in that they are only evaluated in vitro by the capacity of binding GLP-1 receptor, the insulin secretion amount of islet cell tumor and the producing amount of cyclic AMP (cAMP) (Refer to: J. Biol. Chem (1997) 272 21201-21206; Regulatory Peptides (2003) 114 153-158; Trend in Pharmacological Sci. (2003) 24 377-383; WO 03011892A).

In order to overcome the disadvantages of existing technologies, the inventors have been striving for a novel C-terminal truncated Exendin 4 polypeptide fragment with Pro at its C-terminus. It is notable that polypeptide with this structure shortens the peptide chain by about ¼ and facilitates production, but provides a new alternative for diabetes treatment. Furthermore, the truncated Exendin 4 can effectively resist carboxypeptidase, and maintain its hypoglycemic activity for a longer period.

DETAILED DESCRIPTION OF THE INVENTION

In one aspect, the present disclosure provides an Exendin 4 polypeptide fragment and pharmaceutically acceptable salts or esters thereof, which have the sequence represented by formula (I):

$$\text{HGEGTX}_1\text{TSDLSKQX}_2\text{EEEAVX}_3\text{LFIEWLKNGX}_4\text{PX}_5 \quad \text{(I)}$$

Where,
$X_1$ represents Phe or Tyr;
$X_2$ represents Met, Ile or Leu;
$X_3$ represents Lys;
$X_4$ represents Gly=or deletion; and
$X_5$ represents Arg or deletion.

The formula (I), wherein the amino acid residue ($X_1$) of Exendin 4 polypeptide fragment at $6^{th}$ site is preferable Tyr. With respect to pharmacokinetics research, the Phe in molecular is substituted by Tyr facilitating the labeling of $^{125}$I.

The formula (I), wherein the amino acid residue ($X_2$) of Exendin 4 polypeptide fragment at $14^{th}$ site is alternative to Met, Ile or Leu, is preferably Met.

The formula (I), wherein the amino acid residue ($X_4$) of Exendin 4 polypeptide fragment at $30^{th}$ site is preferably a deletion.

Preferably, the polypeptide fragment is: $X_1$ is Tyr, $X_2$ is Met, $X_3$ is Lys, $X_4$ is deletion, $X_5$ is Arg or deletion.

In the present invention, the term "the presented Exendin 4 polypeptide fragment" refers to the truncated Exendin 4 polypeptide whose sequence is shown in formula (I). In the present invention, this polypeptide simply named "E4(f)," "polypeptide fragment" or "the presented polypeptide."

The polypeptide fragment represented by the formula (I), wherein the N-terminal amino group, the C-terminal carboxyl group and the amino acid side-chain groups are either unmodified or modified without basically affecting the activity of the present polypeptide, such as forming the "pharmaceutically acceptable esters." The modification of the amino acid side-chain groups include, but are not limited to, acylation of ε-amino group of lysine, deacylation of N-alkyl of arginine, histidine or lysine. The modification of N-terminal amino groups include, but are not limited to, deamination and modification of N-short chain alkyl, N-short chain dialkyl and N-acyl. The modification of C-terminal carboxyl groups include, but are not limited to, amide, short chain alkyl amide, dialkyl amide and short chain alkyl ester. Preferably, the terminal groups are protect by the protecting group known by those in the art, such as acetyl, trifluoroacetyl, N-(9-fluorenyl) methoxycarbonyl (Fmoc), tert-butoxycarbonyl (Boc), allyloxycarbonyl (Alloc), $C_{1-6}$ alkyl, $C_{2-8}$ alkenyl, $C_{7-9}$ aralkyl, etc. Preferably, the polypeptide fragment represented by the formula (I) in the present invention, wherein the N-terminal amino group, the C-terminal carboxyl group and the amino acid side-chain groups are unmodified, i.e. N-terminal group is still α-amido (—$NH_2$) of His at N-terminus, and C-terminal group is still carboxyl (—COOH) of Pro at C-terminus. Also preferably, C-terminal carboxyl group of Pro is amidated, i.e. —$CONH_2$.

In the present invention, the denotations for the polypeptide, amino acids and chemical groups are well recognized in the art. The abbreviations for amino acids are shown in Table 1. In the present invention, generally the amino acids refer to L-amino acids if not other specific definition.

TABLE 1

The amino acids and their abbreviations

| Amino acids letter code | three letter code | one |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "pharmaceutically acceptable salts" refers to the salts of small acidic or basic compounds combining to polypeptide. The salts formed generally enhance the solubility of polypeptide and have basically no effect on the activity of polypeptide. For example, the acids include hydrochloric acid, phosphoric acid, sulfuric acid, acetic acid, succinic acid, maleic acid, citric acid, etc., which can generally form salts with the polypeptide in the present invention. The bases include the hydroxides of the alkali metal or alkaline-earth metals, ammonium, carbonate, etc., which can generally form salts with the polypeptide in the present invention.

The effect of hypoglycemic levels of the polypeptide in the present invention is validated with the routine methods in the art, such as the experiments of cell biology, the animal experiments, etc. In embodiments of the present invention, in order to overcome the limitations of the experiments in vitro, preferably employed diabetic animal models to assay the effect of hypoglycemic levels, such as db/db II diabetic mice, Goto-Kokizaki (GK) II type rat, diabetic KK mice, alloxan induced diabetic mice. These animal experiments indicate the Exendin 4 polypeptide fragment represented by formula (I) in the present invention, has a continuous effect of sustaining hypoglycemic activity in vivo and can be used for the diabetes treatment.

Wherefore, in another aspect, the present invention provides the pharmaceutical compositions of the Exendin 4 polypeptide fragment represented by formula (I), which can be used for the treatment of diabetics, especially for the treatment of type II diabetics. The pharmaceutical compositions include one or several kinds of Exendin 4 polypeptide fragments in the present invention, preferably only one Exendin 4 polypeptide fragment. This pharmaceutical composition includes one or several kinds of pharmaceutically acceptable thinners, excipients or carriers. Preferably this pharmaceutical compositions supplied as pharmaceutical unit dosage form, such as tablet, pellicle, pill, capsule (including sustained-release and delayed-release forms), powder, granule, tincture, syrup, emulsion, sterile injection solution or suspension, aerosol or liquid spray, drops, injection, automatic injection devices and suppository. In one embodiment, orally administrated as a tablet or a capsule, the active ingredient above mentioned can be combined with a pharmaceutically acceptable and non-toxic inertia carrier, such as ethanol, glycerol, water alone or in combination. The previous patents of WO2004035754A and WO2004036186A announced respectively a dosage form which is applicable for the controlled release dosage form of Exendin 4 polypeptide fragment, preferably this dosage form is recommended for the active polypeptide represented by formula (I) in the present invention (The disclosures of both WO2004035754A and WO2004036186A are incorporated herein by reference in their entirety).

The present invention also provides the application of the compounds or pharmaceutical compositions mentioned above on the drug preparation for diabetes therapy, preferably used for type II diabetes therapy. The pharmaceutical compositions in the present invention are administered by the ways of drug administration which are well-known by those skilled in the art, such as oral delivery, rectal administration, sublingual administration, pulmonary drug delivery, transdermal drug delivery, iontophoresis, vaginal administration and intranasal delivery. Preferably, the pharmaceutical compositions in the present invention are administered by parenteral injection, such as subcutaneous administration, intramuscular administration and intravenous administration. The drug in the present invention can adjust insulin and consequently maintain lastingly the blood sugar at normal levels. The administration dosage may be varied by the dosage form, expected effect duration and therapy objectives. The clinical dosage may be conveniently determined by the physicians according to the actual situation (for example, the patient's state of illness and body weight, etc.). For the normal adults, the administration dosage ranges from 0.1 μg to 100 μg per day, preferably ranges from 1 μg to 20 μg, or preferably ranges from 5 μg to 10 μg. The dosage can also be determined by referencing to the administration dosage of commercially available Exendin 4 polypeptide drug.

The present invention also provides a chemically synthetic polypeptide method. The chemically synthetic polypeptide method is familiar to those skilled in the art. The detail scheme can be carried out according to the method in the following literature, such as the solid phase synthesis method of polypeptide referring to "Solid Phase Peptide Synthesis, 2nd Ed" by J. M. Steward and J. D. Young, Pierce Chemical Company, Rockford, Illinois (1984) and "Hormonal Proteins and Peptides" by J. Meienhofer, Volume II, Academic Press, New York (1973). The liquid phase synthesis method of peptide referring to "The Peptides" by E. Schroder and K. Lubke, Volume I, Academic Press, New York (1965). The disclosures of all of the references are incorporated herein by reference in their entirety. In one embodiment, the present invention preferably employs a solid phase synthesis method of polypeptide.

In another aspect, the present invention provides a nucleic acid sequence of the E4 (f) polypeptide fragment using the codon usage bias in E. coli. For example, if the nucleic acid sequence of the polypeptide in the present invention is expressed in E. coli, the expressing product is preferably optimized by the codon usage bias in E. coli.

The present invention also provides a genetic engineering method for producing the polypeptide mentioned above. This method includes: a) the fermentation of the host cell expressing the polypeptide in the present invention; and b) the extraction and purification of expressing product. This method further includes the cleavage processes of expressing product. The expression level of polypeptides with medium molecular weight (20-60 amino acid residues) is usually low and easy to be degraded. So one approach is to link the target polypeptide gene to carrier protein gene, and the target protein is expressed as fusion protein. After that, the target protein can be obtained by cleavage, extraction and purification from fusion protein using either a chemical or an enzymatic method. The disadvantage of this method is that the protein yield is low and the procedure is complicated. Another approach is based on the amino acids sequence of polypeptide, Multiple target gene copies are tandemly linked, and driven by appropriate promoter. The tandemly linked target protein can be prepared by cleavage. This approach is successful in many practical cases of polypeptides preparation, such as human insulin (Proc, Natl. Acad. Sci. USA. 1984 81 4627-4631), calcitonin (JP62-226998), GLP-1(WO95/17510). The advantage of this approach is that the expression protein yield is very high. Preferably, the polypeptide in the present invention is expressed using the multiple tandemly linked genes method as described above. The linked polypeptides are cleaved using routine methods in the art. For example, after protecting the Lys residue with citraconic anhydride, the multimeric polypeptides are cleaved at Arg site with trypsin, followed by removing citraconic acid group by acid treatment (Refer to: J. D. Baxter. et al., Nature 1980 285 456-461; JP62-226998). In one preferable embodiment, as shown in FIG. 1, the method described above includes: a) fermentation of bacterial cells expressing the polypeptides in the present invention; b) harvesting bacterial cells; c) cell lysis; d) extraction of the multimeric polypeptides; e) refolding of prepared polypeptides; f) cleavage; and g) purification of final polypeptides using high-pressure liquid chromatography (HPLC).

The target polypeptides (with 20-60 amino acid residues) expressed by genetic engineering techniques can be obtained only if they are linked to a carrier protein. The yield of the target protein is very low because the fusion protein molecular only contains one target polypeptide molecular, which only accounts for about 10% of fusion protein. Furthermore, many other non-target proteins are also obtained after fusion protein cleavage, which makes it is very difficult to purify the target polypeptides. In the present invention, multiple polypeptides genes are tandemly linked, the expressed fusion proteins are only comprised of target polypeptides. The cleaved polypeptide is only in a single form and the yield is 10 times higher than the former method, which make the purification procedure become quite easy. In the present invention, the $X_3$ site presents as Lyr, the fusion protein only cleaved at intermolecular sites (Arg site) ensuring the integrity of $E_4(f)$.

The Pro residues at C-terminus in $E_4(f)$ are resistant against carboxypeptidase A and B, which will enhance the stability of the molecular.

Indeed, as an intermediate of $E_4(f)$, Arg residue in $E_4(f)$Arg is rapidly removed by carboxypeptidase B in blood and $E_4(f)$Arg is hydrolyzed to form $E_4(f)$, both $E_4(f)$ and $E_4(f)$Arg are effective.

The following examples are offered to illustrate the present invention and should not be construed in any way as limiting the scope of this invention. In addition, the disclosures of all of the references are incorporated herein by reference in their entirety. The present invention will be more clearly understood from a consideration of the following embodiments, taken in conjunction with the accompanying drawings. Therefore, it must be understood that the following embodiments are offered to illustrate the present invention and should not be taken in any way as limiting the scope of this invention. According to the present invention, various modifications of the present invention, in addition to those described herein, will become apparent to those skilled in the art. In addition, the disclosures of all of the references are incorporated herein by reference in their entirety.

EXAMPLES

Example 1

Figure 1:
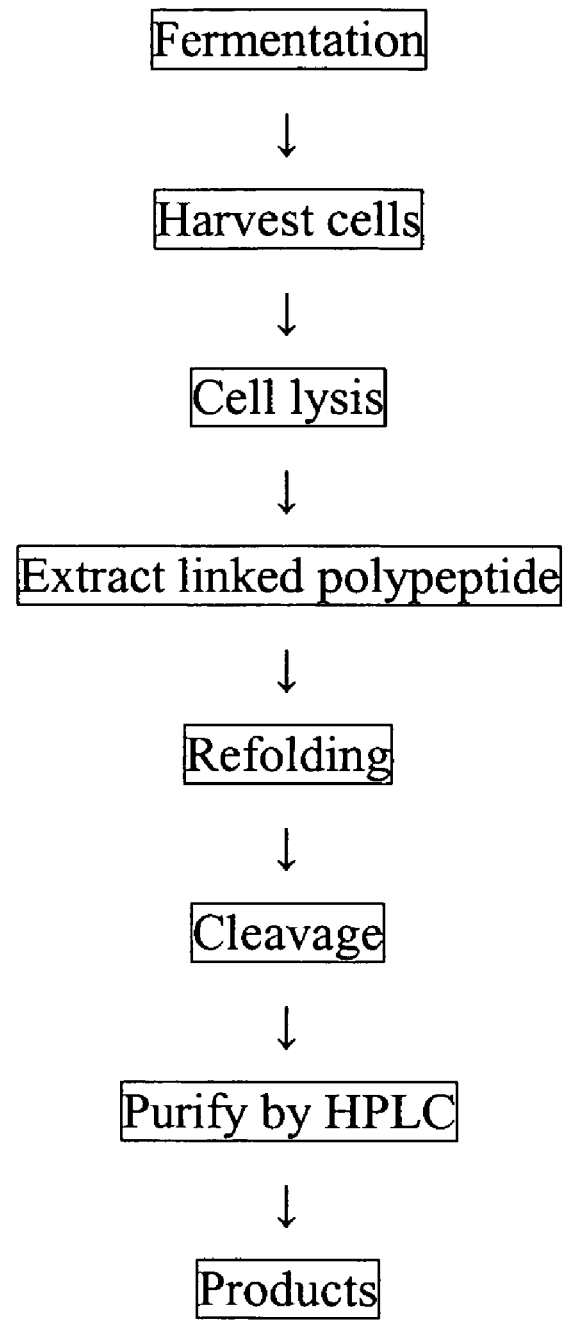
FIG. 1. Flow chart of Exendin 4 polypeptide fragment preparation using genetic engineering method.
Figure 2:
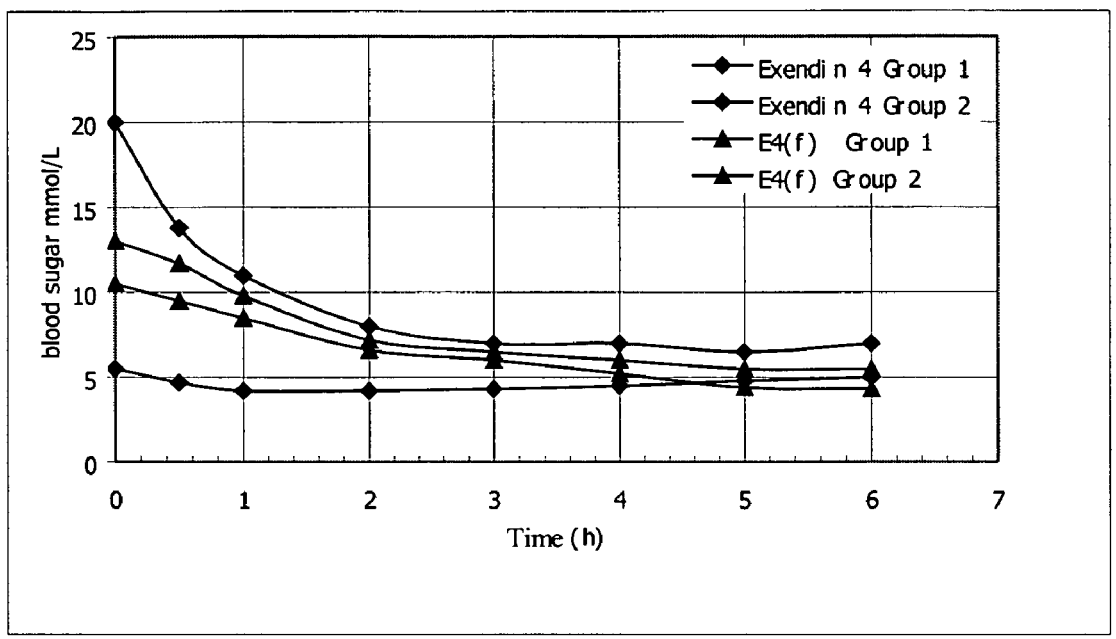
FIG. 2. Comparison of the sustained hypoglycemic activity of Exendin 4 polypeptide fragment having the sequence of SEQ ID NO. 2 with Exendin 4.
Figure 3:
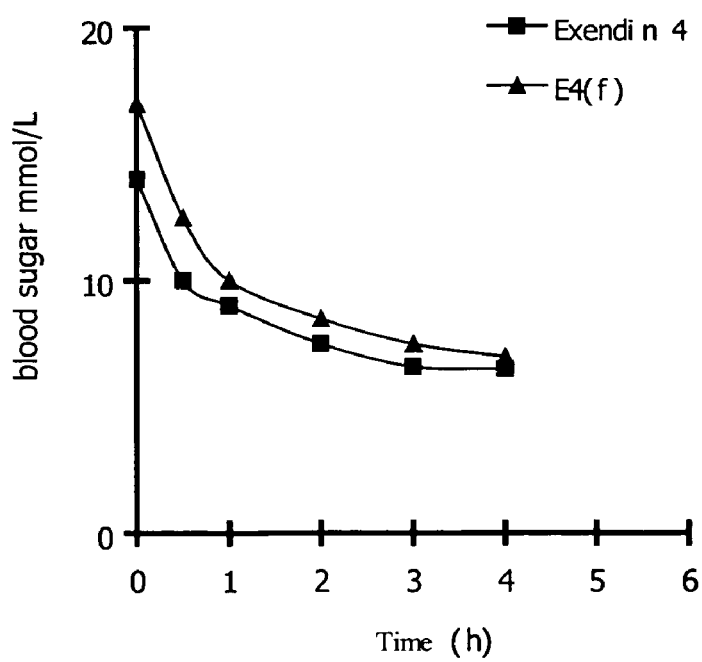
FIG. 3. The hypoglycemic activity of Exendin 4 polypeptide fragment having the sequence of SEQ ID NO. 2 on db/db II diabetic mice.

The solid phase synthesis method of Exendin 4 polypeptide variants.

The polypeptides are synthesized by solid phase peptide synthesis methodology using the multiple, fully automatic SyRo II peptide synthesizer. N-(9-fluorenyl) methoxycarbonyl (Fmoc) is used to protect the α-amido of amino acid. Other protecting groups are also used to protect the amino acid side chains, such as tert-butyl for Asp, Glu, Ser and Thr; Trityl (Trt) for Asn, Gln and His; tert-butoxycarbonyl(Boc) for Lys and Trp; 2,2,5,7,8,-5-pentamethyl-chroman-6-sulphonyl (Pmc) for Arg. By using N,N'-diisopropylcarbodiimide/1-hydroxybenzotriazole as activating reagent, the protected amino acids are conjugated one by one, 40 minutes for each conjugation reaction. In the presence of 15% ethanedithiol/dimethyl sulphide/anisole(1:1:1v/v/v), the polypeptides react with 85% trifluoroacetic acid at room temperature for 120 min, and then cleaved from resins and deprotected simultaneously. After being precipitated by anhydrous aether, the precipitate is washed with anhydrous aether several times in order to remove mercaptan completely. Then the polypeptides are precipitated with water/tert-butyl alcohol (1:1), and lyophilized to crude polypeptides. The crude polypeptides are purified by reverse phase HPLC on a 37-42% acetonitrile/0.9% trifluoroacetic acid (TFA) gradation within 30 minutes. The eluted solution is concentrated and lyophilized. The purity of final white solid product is more than 97%.

The solid phase Exendin 4 polypeptide variants having the sequences of SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11 and SEQ ID NO. 12 were respectively prepared according to the method as mentioned in example 1.

Example 2

Production procedure of Exendin 4 polypeptide variants by bioengineering

1) Chemical synthesis of four gene fragments (Shanghai Biocolor Bioscience & Technology Company, China)
    (1) SEQ ID NO. 17;
    (2) SEQ ID NO. 18;
    (3) SEQ ID NO. 19;
    (4) SEQ ID NO. 20.

2) Ligations of gene fragments:

50 μl of water is added to four synthesized genes ($A_{260nm}$=2), labeled as (1), (2), (3) and (4) respectively, remove 2 μl of (1) and (4) to one microtube and mix, then remove 2 μl of (2) and (3) to another microtube and mix. 1 μl of 10×T4 polynucleotide kinase buffer, 1 μl ATP (0.1 mol/L) and 1 μl T4 polynucleotide kinase are added to both microtubes, keep at 37° C. for 30 minutes, then keep in 95° C. water bath for 5 minutes, cool down to room temperature, mix the components from the two microtubes, and then add 2 μl 10×ligase buffer, 1 μl ATP (0.1 mol/L) and 2 μl T4 ligase, keep the microtubes at 16° C. for 2 hours, the ligated fragments are then purified with DNA fraction kit (Shanghai Biocolor Bioscience & Technology Company, China; Promega company, USA), after digested with EcoRI and SalI, the fragment is then analyzed by electrophoresis.

3) Cloning:

Add 1 μg of pUC 18 plasmid (Shanghai Biocolor Bioscience & Technology Company, China) to a clean tube. Add 1 μl 10×restriction enzyme buffer. Add 1 μl of EcoRI and SalI enzyme, respectively. Incubate at 37° C. for 30 min. Extract with phenol:chloroform. Centrifuge the microtube to separate the phases. Remove the supernatant to a clean tube. Extract with chloroform again. Remove the chloroform by centrifugation. Precipitate the DNA with 60% isopropanol. Centrifuge the tube to collect the DNA, then dry the pellet and store DNA until use. Mix the EcoRI and SalI digested DNA fragment prepared in step (2) with the same enzymes digested plasmid described above. Add 1 μl of 10×ligation buffer, 1 μl ATP and 2 μl T4 ligase. Incubate at 16° C. for 12 hours. The preparation of *E. coli* strain JM 109 competent cells are made by using routine methods. The ligation-reaction mixture described above is used for the transform. Positive colonies of transformants are picked and then plasmids are extracted.

4) Linkage:

The vector containing the variant polypeptide genes from step (3) is double digested with Bgl II and Sal I, and this variant polypeptide-containing DNA fragments are then extracted. Also, the vector from step (3) is double digested with Bam HI and Sal I, the vector containing two variant polypeptide genes is obtained by ligating the two digested variant polypeptide-containing DNA fragments. This resulting vector is further digested with Bgl HI and Sal I, and a fragment containing two genes is obtained, this fragment is ligated to the two-genes-containing vector which is previously digested with Bam HI and Sal I, which makes the formation of four-genes-containing vector. Likewise, eight, sixteen or thirty-two-gene-containing vectors can be obtained by this method.

5) Transformation:

Mix the plasmid containing variant polypeptide with the competent cell of JM 109 E. coli. Keep on wet ice for 30 minutes. Heat shock the cells for 2 minutes in a water bath at exactly 42° C. Transfer onto wet ice. Plate transformation culture onto the LB plates containing 1% agarose and 50 μg/ml ampicillin. Incubate the plates overnight at 37° C. Pick single colonies of transformants into a flask with LB culture media containing 50 μg/ml ampicillin. Grow the cultures with vigorous shaking at 37° C. overnight. Add 0.3 ml of 50% glycerol to 0.7 ml of the overnight cultures, mix thoroughly and store at −85° C. until use. 6) Production procedure for variants polypeptide by fermentation method (Flow chart shown in FIG. 1)

Firstly, prepare 1000 ml LB culture media (10 g Bacto-tryptone, 5 g Bacto-yeast extract, 5 g NaCl) and autoclave at 120° C. for 30 minutes. Cool to room temperature before adding ampicillin (final concentration 100 μg/ml). Inoculate 1 ml cell culture from stock tubes with glycerol prepared in step (5). Grow the cultures with vigorous shaking at 37° C. overnight. Harvest the cell culture by centrifugation at 5,000 rpm. After freezing at −35° C., thaw the cell culture and add 6M guanidine hydrochloride. Homogenize samples and extract the linked polypeptide, collect the supernatant by centrifugation at 18,000 rpm. Remove the supernatant to a new tube, and add the dialysis buffer (10 mM phosphate buffer, pH 7.2; 0.1% mercaptoethanol) to refold the polypeptides. Isolate the linked polypeptides by centrifugation. Then cleave the liked polypeptide according to the methods described by J. D. Baxter et al. (Nature 1980, 285, 456-461). Dissolve the linked polypeptides in water, add $Na_2CO_3$ to pH 8.5. Add citraconic anhydride to dissolve the inclusion body completely at pH8.5. Vortex and incubate the tube at room temperature for 2 hours. Add trypsin and carboxypeptidase B. After incubated at 37° C. for 2 hours, the linked polypeptide is obtained. Add 3N hydrochloric acid to adjust pH value at 3, vortex for 4 hours, deprotect the protecting group of citraconic acid to get the final purified Exendin 4 polypeptide having the sequence of SEQ ID NO. 2 in the present invention. Completion of reaction can be monitored by HPLC.

The Exendin 4 polypeptide fragments having the sequences of SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11 and SEQ ID NO. 12 were respectively prepared by the same method as mentioned in example 2.

The SEQ ID Numbers of the polypeptide variants and the corresponding gene fragments are as follows:

The corresponding gene fragment of the polypeptide having the sequence of SEQ ID NO. 1: (1) SEQ ID NO. 13; (2) SEQ ID NO. 14; (3) SEQ ID NO. 15; (4) SEQ ID NO. 16.

The corresponding gene fragment of the polypeptide having the sequence of SEQ ID NO. 3: (1) SEQ ID NO. 21; (2) SEQ ID NO. 22; (3) SEQ ID NO. 23; (4) SEQ ID NO. 24.

The corresponding gene fragment of the polypeptide having the sequence of SEQ ID NO. 4: (1) SEQ ID NO. 25; (2) SEQ ID NO. 26; (3) SEQ ID NO. 27; (4) SEQ ID NO. 28.

The corresponding gene fragment of the polypeptide having the sequence of SEQ ID NO. 5: (1) SEQ ID NO. 29; (2) SEQ ID NO. 30; (3) SEQ ID NO. 31; (4) SEQ ID NO. 32.

The corresponding gene fragment of the polypeptide having the sequence of SEQ ID NO. 6: (1) SEQ ID NO. 33; (2) SEQ ID NO. 34; (3) SEQ ID NO. 35; (4) SEQ ID NO. 36.

The corresponding gene fragment of the polypeptide having the sequence of SEQ ID NO. 7: (1) SEQ ID NO. 37; (2) SEQ ID NO. 38; (3) SEQ ID NO. 39; (4) SEQ ID NO. 40.

The corresponding gene fragment of the polypeptide having the sequence of SEQ ID NO. 8: (1) SEQ ID NO. 41; (2) SEQ ID NO. 42; (3) SEQ ID NO. 43; (4) SEQ ID NO. 44.

The corresponding gene fragment of the polypeptide having the sequence of SEQ ID NO. 9: (1) SEQ ID NO. 45; (2) SEQ ID NO. 46; (3) SEQ ID NO. 47; (4) SEQ ID NO. 48.

The corresponding gene fragment of the polypeptide having the sequence of SEQ ID NO. 10: (1) SEQ ID NO. 49; (2) SEQ ID NO. 50; (3) SEQ ID NO. 51; (4) SEQ ID NO. 52.

The corresponding gene fragment of the polypeptide having the sequence of SEQ ID NO. 11: (1) SEQ ID NO. 53; (2) SEQ ID NO. 54; (3) SEQ ID NO. 55; (4) SEQ ID NO. 56.

The corresponding gene fragment of the polypeptide having the sequence of SEQ ID NO. 12: (1) SEQ ID NO. 57; (2) SEQ ID NO. 58; (3) SEQ ID NO. 59; (4) SEQ ID NO. 60.

Example 3

The sustained hypoglycemic activity assay of Exendin 4 polypeptide fragment.

KK type II diabetic mice (purchased from Shanghai Laboratory Animal Center, Chinese Academy of Sciences, China) with 50 g body weight are subjected to fasting for 2 hours, and are divided into four groups. Two groups are injected with 2 μg Exendin 4, the other two groups are injected with 2 μg Exendin 4 polypeptide fragment presented in the invention. Twenty microliter blood samples are obtained from fasted animals at 0, 0.5, 1, 2, 3, 4, 5 and 6 h time points respectively after administration of the test substance. The sustained hypoglycemic activity is analyzed by using the blood sugar assay kit (purchased from Shanghai Institute of Biological Products, China). The corresponding results of the Exendin 4 polypeptide fragments having the sequences of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11 and SEQ ID NO. 12 are shown in FIG. 7, FIG. 2, FIG. 12, FIG. 17, FIG. 22, FIG. 27, FIG. 32, FIG. 37, FIG. 42, FIG. 47, FIG. 52 and FIG. 57 respectively.

Example 4

The hypoglycemic activity assay of Exendin 4 polypeptide fragment on db/db II diabetic mice.

The db/db II diabetic mice (purchased from Shanghai Laboratory Animal Center, Chinese Academy of Sciences and Yangzhou University, China) with 50 g body weight are subjected to fasting for 2 hours, the test animals were administrated by subcutaneous injection of Exendin 4 polypeptide fragment in a dose of 2 µg. 20 µl blood samples were obtained from fasted animals at 0, 0.5, 1 and 2 hours time points respectively after administration of the test substance. The sustained hypoglycemic activity is analyzed by using the blood sugar assay kit (purchased from Shanghai Institute of Biological Products, China). The corresponding results of the Exendin 4 polypeptide fragments having the sequences of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11 and SEQ ID NO. 12 are shown in FIG. 8, FIG. 3, FIG. 13, FIG. 18, FIG. 23, FIG. 28, FIG. 33, FIG. 38, FIG. 43, FIG. 48, FIG. 53, FIG. 58 respectively.

Example 5

The postprandial hypoglycemic activity of Exendin 4 polypeptide fragment on Goto-Kokizaki type II diabetic rat.

Figure 4:
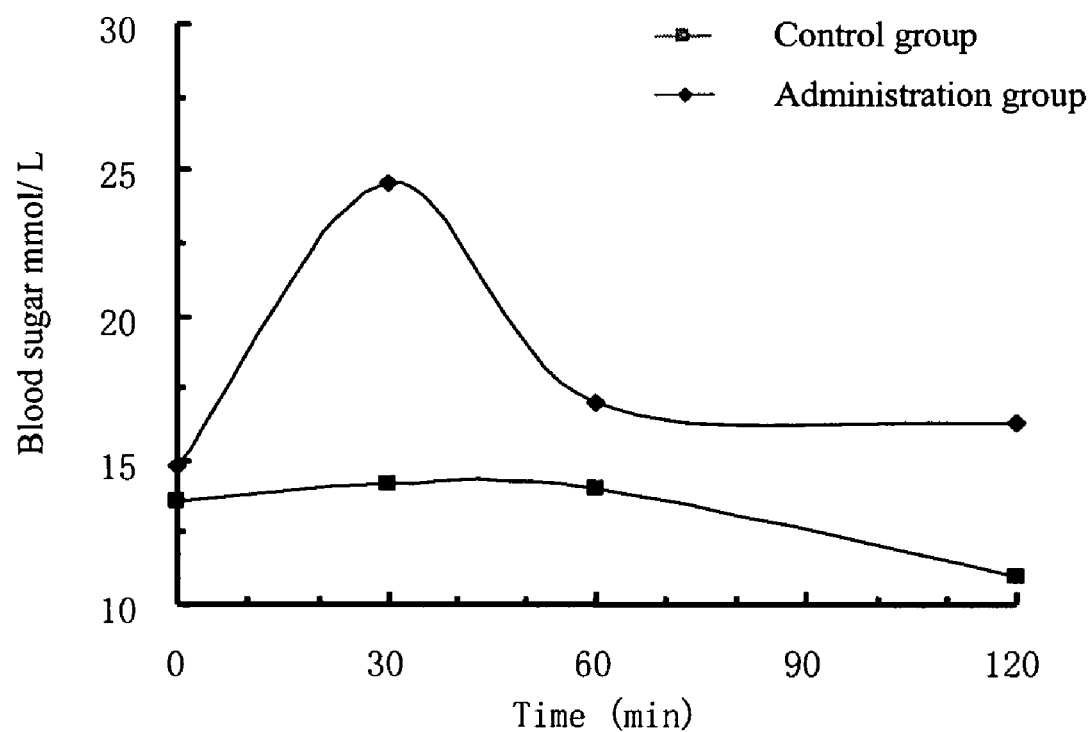
FIG. 4. The postprandial hypoglycemic activity of Exendin 4 polypeptide fragment having the sequence of SEQ ID NO. 2 on Goto-Kokizaki type II diabetic rat. The curve 1 indicates control group. The curve 2 indicates administration group.
Figure 5:
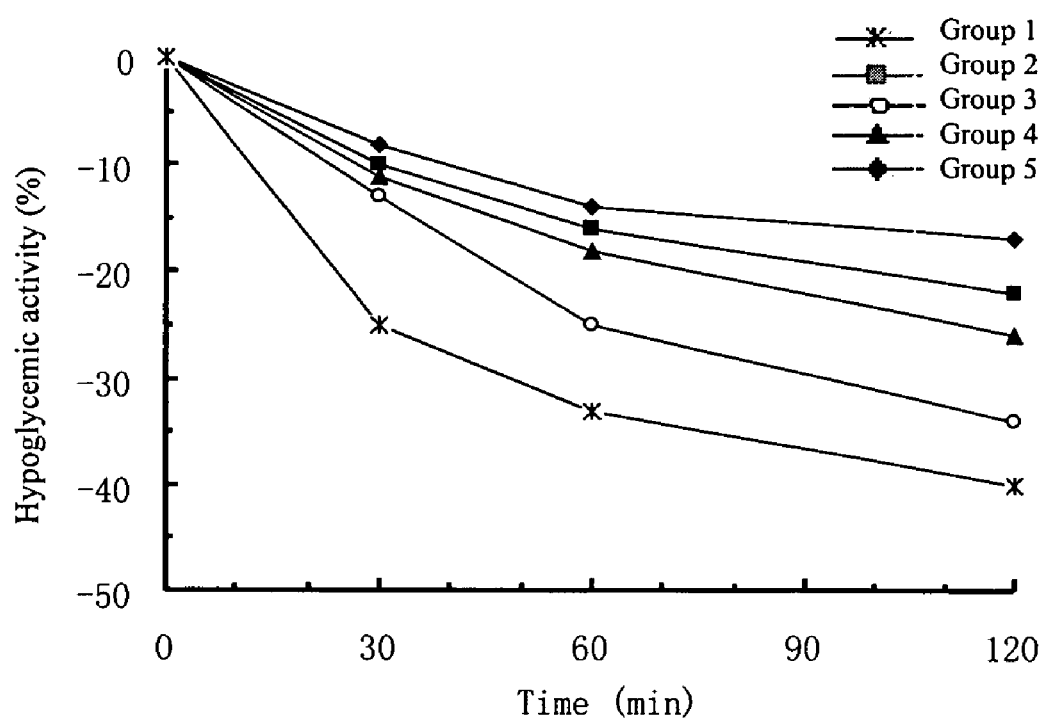
FIG. 5. The hypoglycemic activity of Exendin 4 polypeptide fragment having the sequence of SEQ ID NO. 2 on alloxan induced diabetic mice.

Five-month-old (body weight 470 g) Goto Kokizaki diabetic rat (purchased from Shanghai Laboratory Animal Center, Chinese Academy of Sciences, China) are taken for the operative procedure. After subjecting to fasting for 2 hours, the test animals were administrated by intraperitoneal injection of 20% glucose in a dose of 1 ml and by subcutaneous injection of Exendin 4 polypeptide fragment in a dose of 5 µg. The control group received only glucose. Twenty microliter blood samples were obtained from fasted animals at 0, 0.5, 1 and 2 hours time points respectively after administration of the test substance. The sustained hypoglycemic activity is determined by using the blood sugar assay kit (purchased from Shanghai Institute of Biological Products, China). The results are shown in FIG. 4. The curve 1 indicates the control group. The curve 2 indicates the administration group.

The corresponding results of the Exendin 4 polypeptide fragments having the sequences of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11 and SEQ ID NO. 12 are shown in FIG. 9, FIG. 4, FIG. 14, FIG. 19, FIG. 24, FIG. 29, FIG. 34, FIG. 39, FIG. 44, FIG. 49, FIG. 54, FIG. 59 respectively.

Example 6

The hypoglycemic activity of Exendin 4 polypeptide fragment on alloxan induced diabetic mice.

Eight-week-old (20 g body weight) mice are taken for the operative procedure. Experimental diabetes in mice was induced by (16 mg/ml) 0.1 ml alloxan by tail vein injection. Animals are divided into five groups. 48 hours later, 2 µg Exendin 4 polypeptide fragment was injected. Twenty microliter blood samples were obtained from fasted animals at 0, 0.5, 1 and 2 hours time points respectively after administration of the test substance. The hypoglycemic activity is determined by using the blood sugar assay kit (purchased from Shanghai Institute of Biological Products). The significant hypoglycemic activity was observed in all five groups of diabetic mice.

The corresponding results of the Exendin 4 polypeptide fragments having the sequences of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11 and SEQ ID NO. 12 are shown in FIG. 10, FIG. 5, FIG. 15, FIG. 20, FIG. 25, FIG. 30, FIG. 35, FIG. 40, FIG. 45, FIG. 50, FIG. 55, FIG. 60 respectively.

Example 7

The insulin secretion stimulation by Exendin 4 polypeptide fragment.

Figure 6:
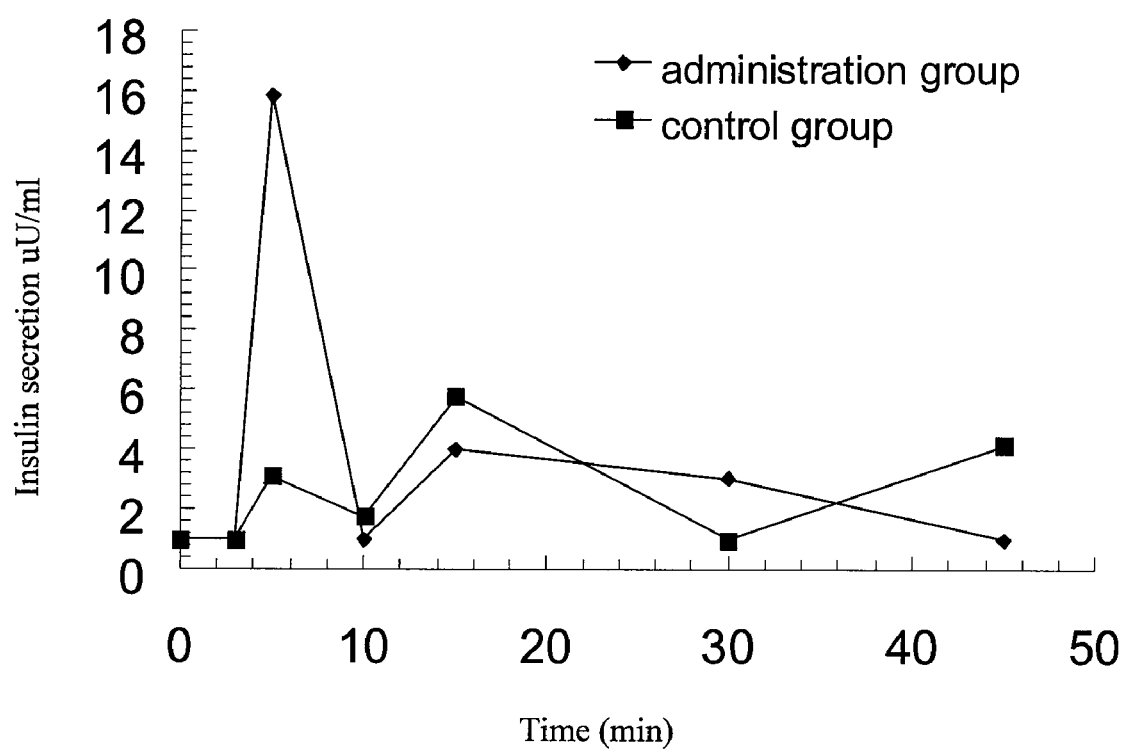
FIG. 6. The insulin secretion stimulated by Exendin 4 polypeptide fragment having the sequence of SEQ ID NO. 2. The curve 1 indicates administration group. The curve 2 indicates blank control group.
Figure 7:
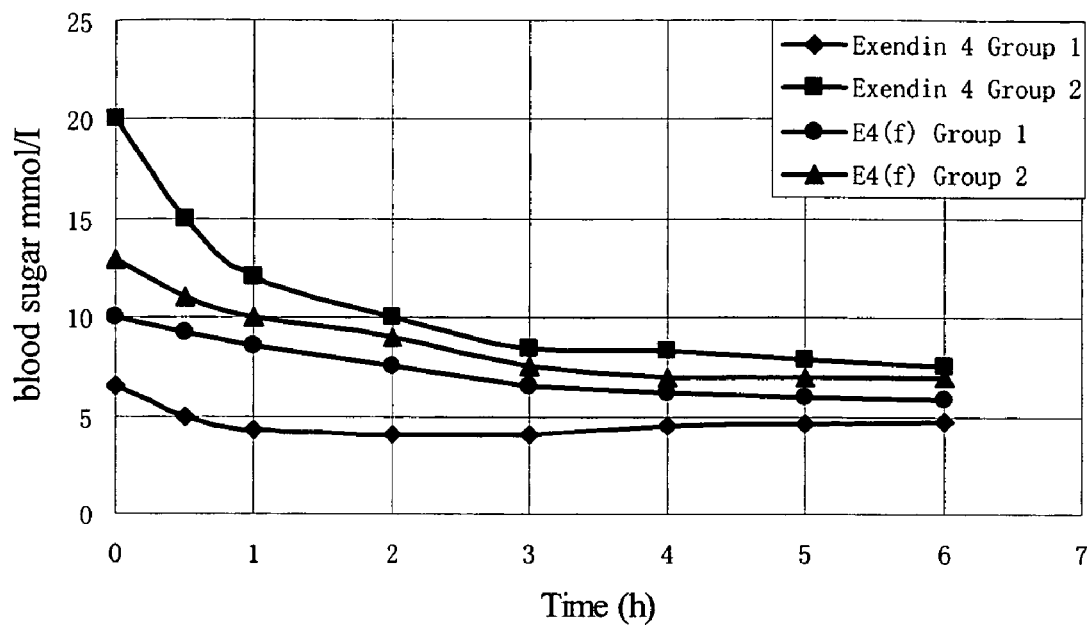
FIG. 7. Comparison of the sustained hypoglycemic activity of Exendin 4 polypeptide fragment having the sequence of SEQ ID NO. 1 with Exendin 4.
Figure 8:
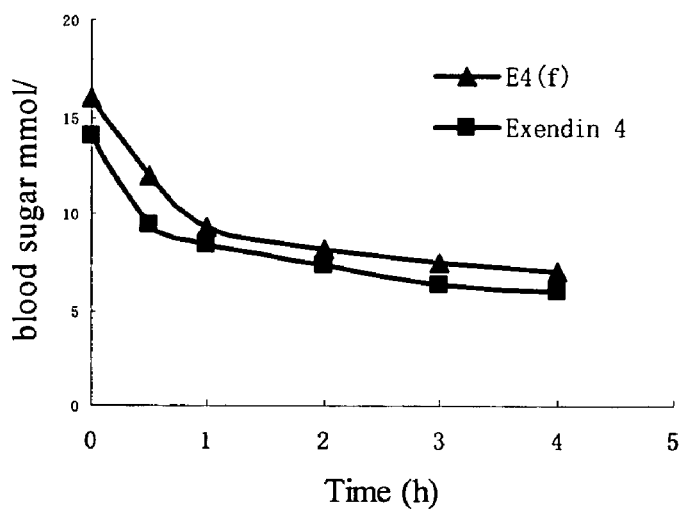
FIG. 8. The hypoglycemic activity of Exendin 4 polypeptide fragment having the sequence of SEQ ID NO. 1 on db/db II diabetic mice.
Figure 9:
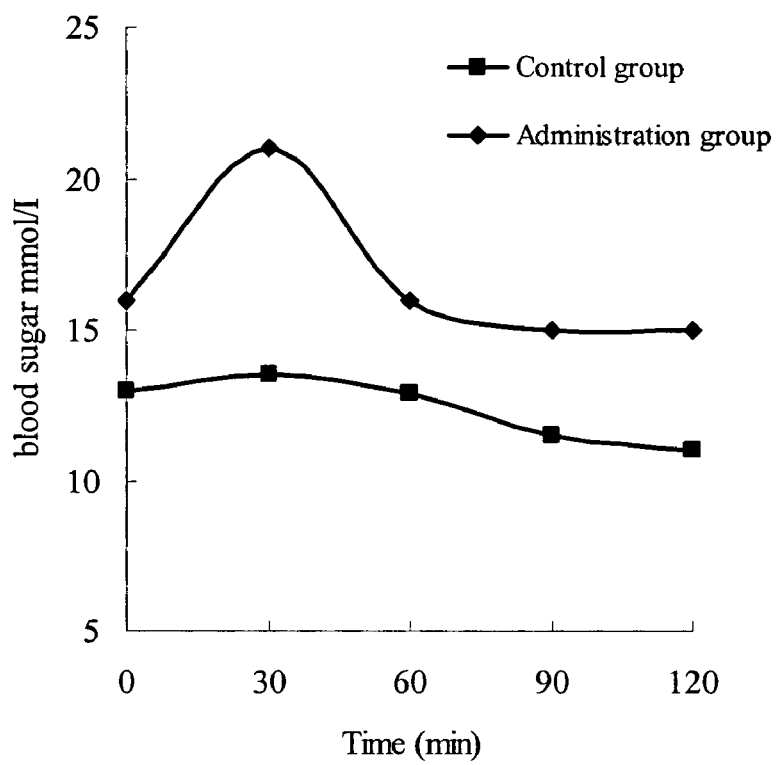
FIG. 9. The postprandial hypoglycemic activity of Exendin 4 polypeptide fragment having the sequence of SEQ ID NO. 1 on Goto-Kokizaki type II diabetic rat. The curve 1 indicates control group. The curve 2 indicates administration group.
Figure 10:
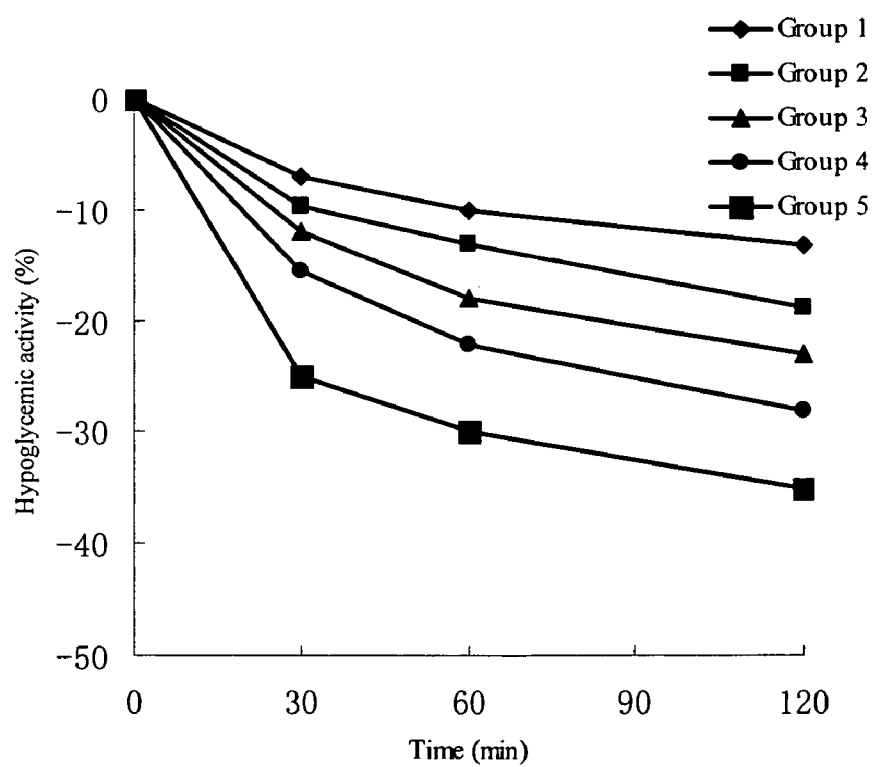
FIG. 10. The hypoglycemic activity of Exendin 4 polypeptide fragment having the sequence of SEQ ID NO. 1 on alloxan induced diabetic mice.
Figure 11:
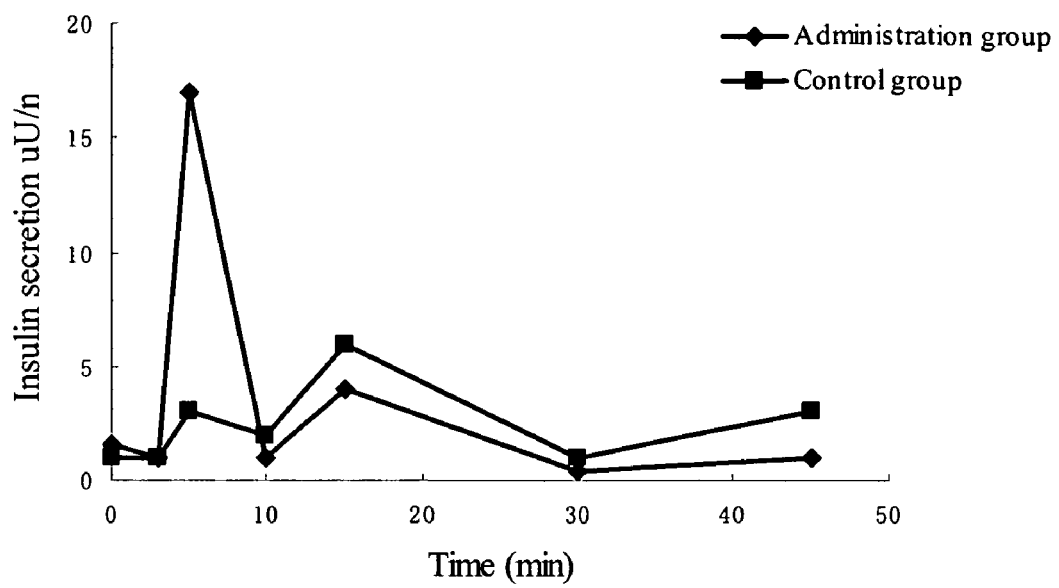
FIG. 11. The insulin secretion stimulated by Exendin 4 polypeptide fragment having the sequence of SEQ ID NO. 1. The curve 1 indicates administration group. The curve 2 indicates blank control group.
Figure 12:
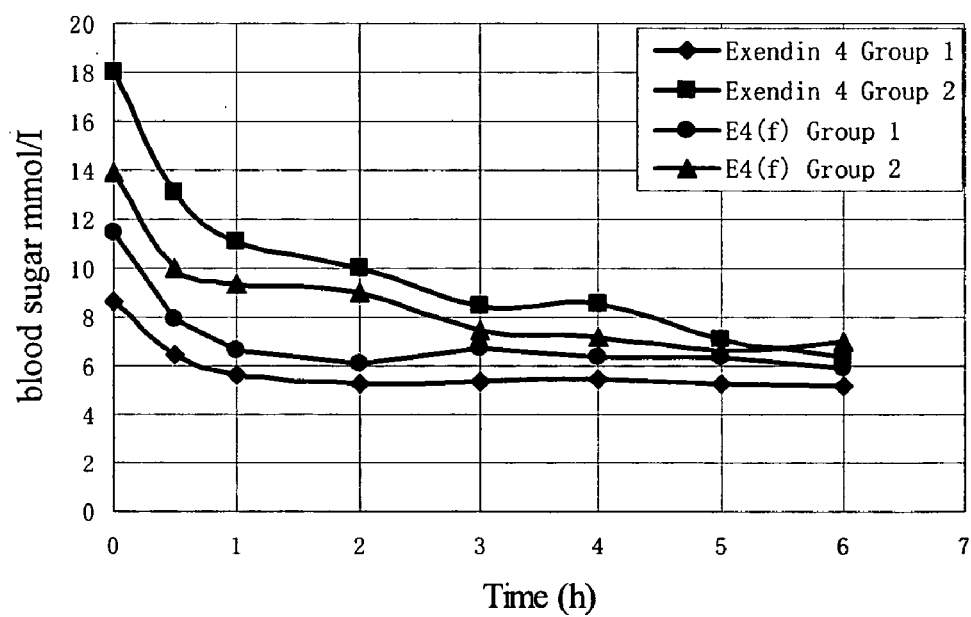
FIG. 12. Comparison of the sustained hypoglycemic activity of Exendin 4 polypeptide fragment having the sequence of SEQ ID NO. 3 with Exendin 4.
Figure 13:
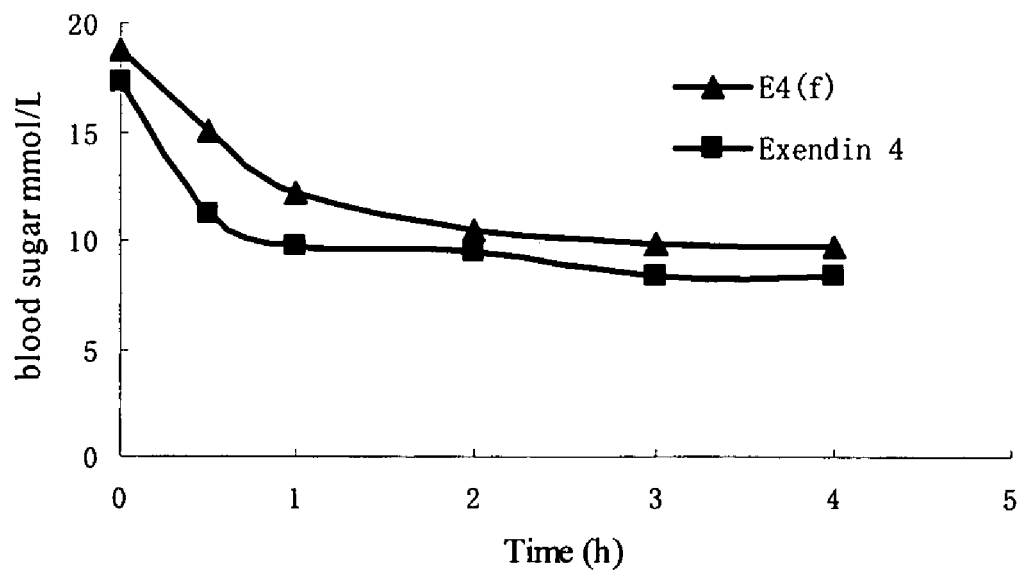
FIG. 13. The hypoglycemic activity of Exendin 4 polypeptide fragment having the sequence of SEQ ID NO. 3 on db/db II diabetic mice.
Figure 14:
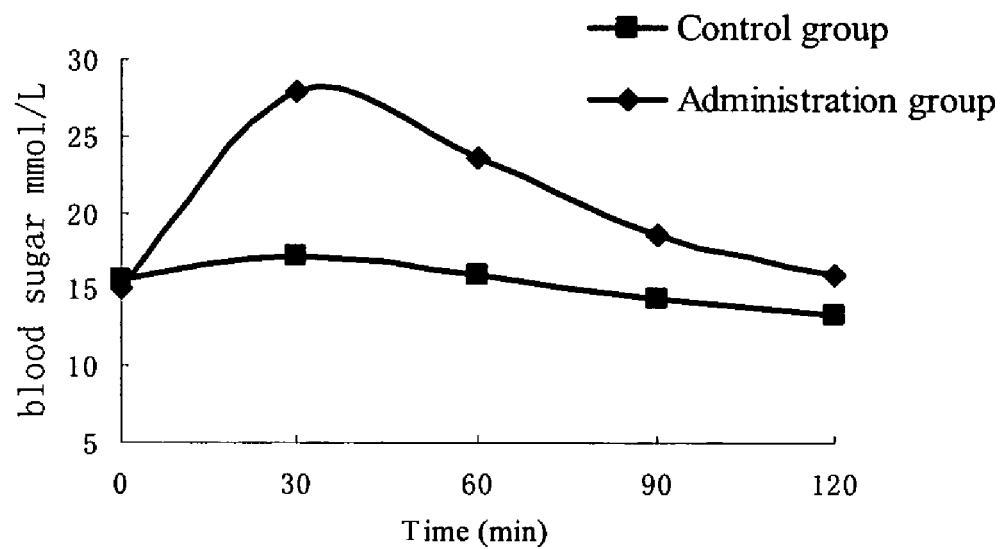
FIG. 14. The postprandial hypoglycemic activity of Exendin 4 polypeptide fragment having the sequence of SEQ ID NO. 3 on Goto-Kokizaki type II diabetic rat. The curve 1 indicates control group. The curve 2 indicates administration group.
Figure 15:
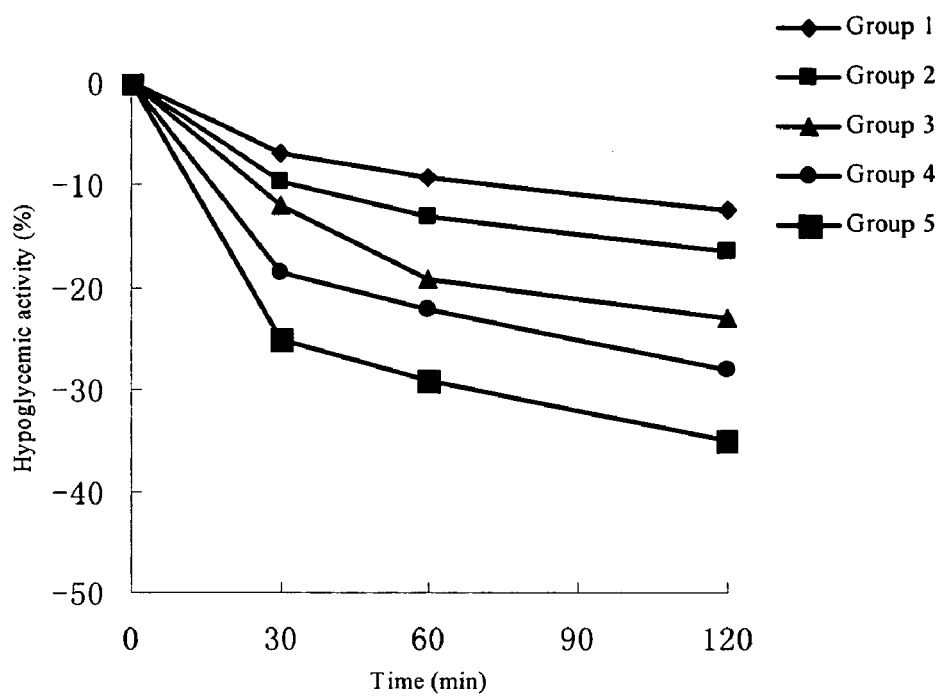
FIG. 15. The hypoglycemic activity of Exendin 4 polypeptide fragment having the sequence of SEQ ID NO. 3 on alloxan induced diabetic mice.
Figure 16:
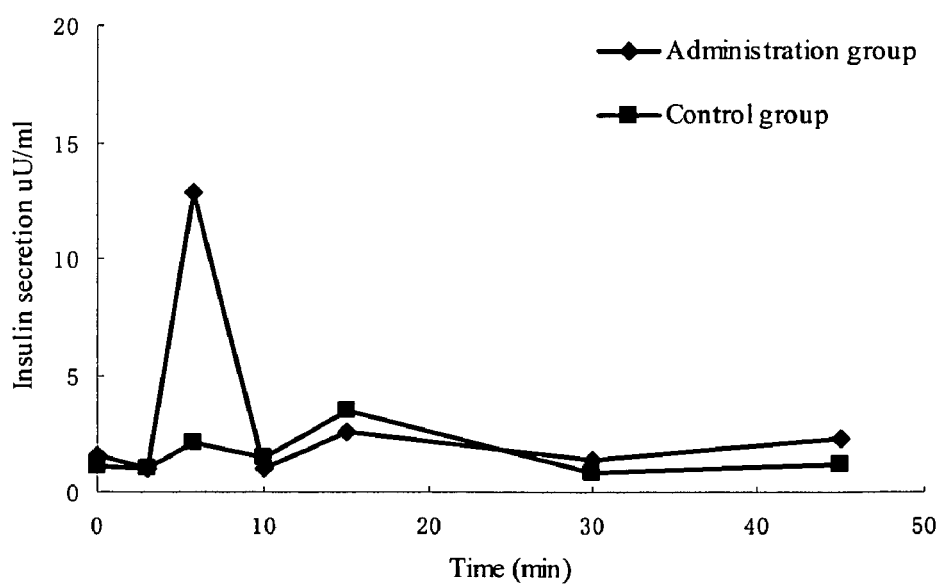
FIG. 16. The insulin secretion stimulated by Exendin 4 polypeptide fragment having the sequence of SEQ ID NO. 3. The curve 1 indicates administration group. The curve 2 indicates blank control group.
Figure 17:
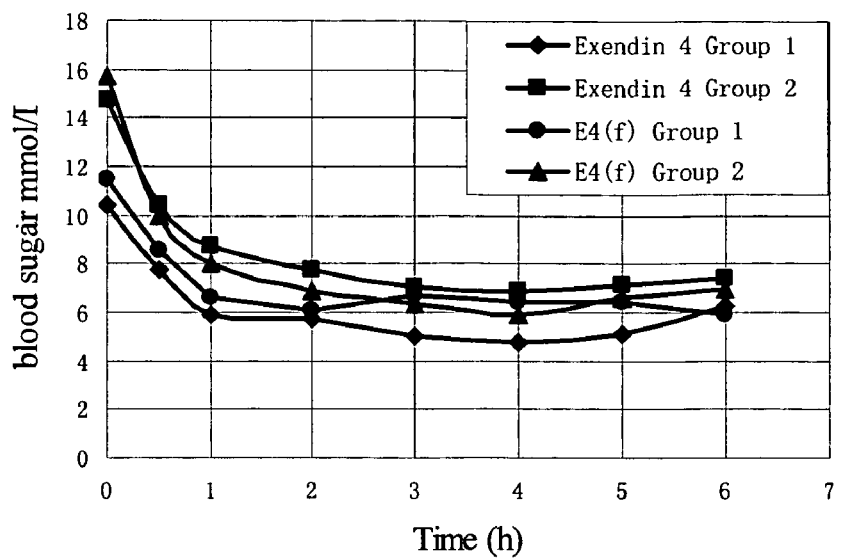
FIG. 17. Comparison of the sustained hypoglycemic activity of Exendin 4 polypeptide fragment having the sequence of SEQ ID NO. 4 with Exendin 4.
Figure 18:
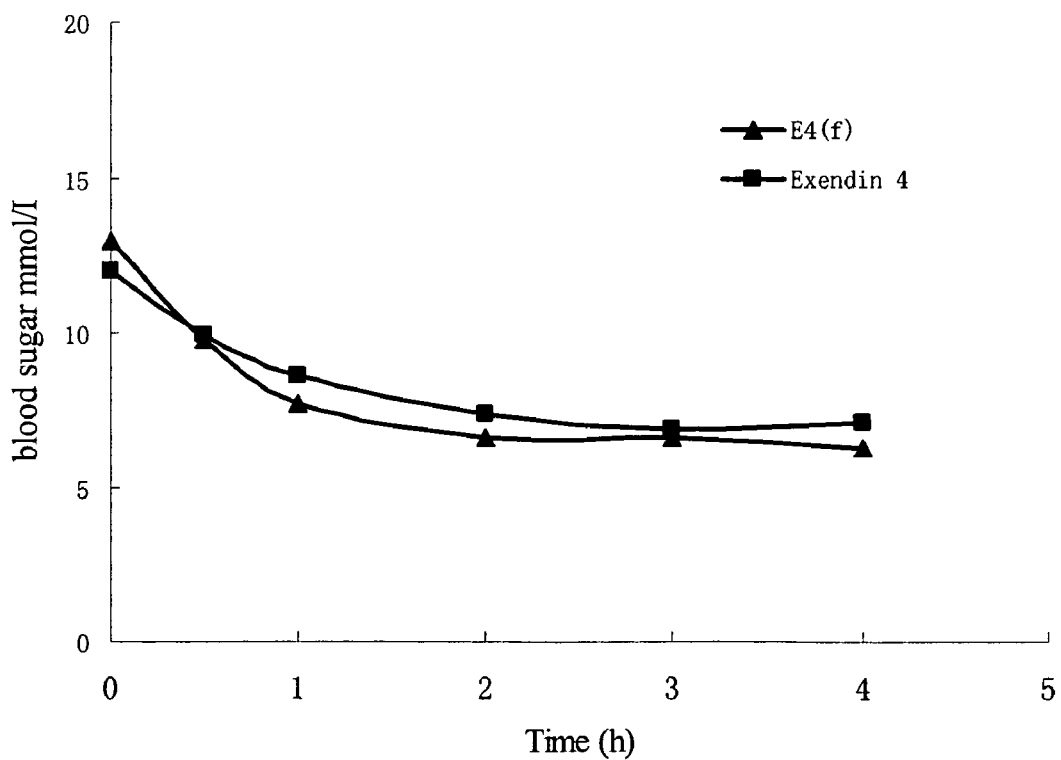
FIG. 18. The hypoglycemic activity of Exendin 4 polypeptide fragment having the sequence of SEQ ID NO. 4 on db/db II diabetic mice.
Figure 19:
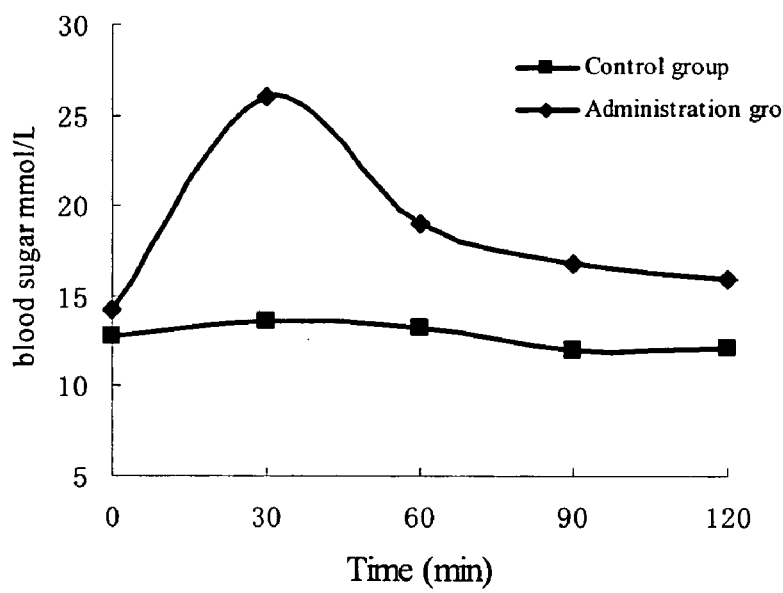
FIG. 19. The postprandial hypoglycemic activity of Exendin 4 polypeptide fragment having the sequence of SEQ ID NO. 4 on Goto-Kokizaki type II diabetic rat. The curve 1 indicates control group. The curve 2 indicates administration group.
Figure 20:
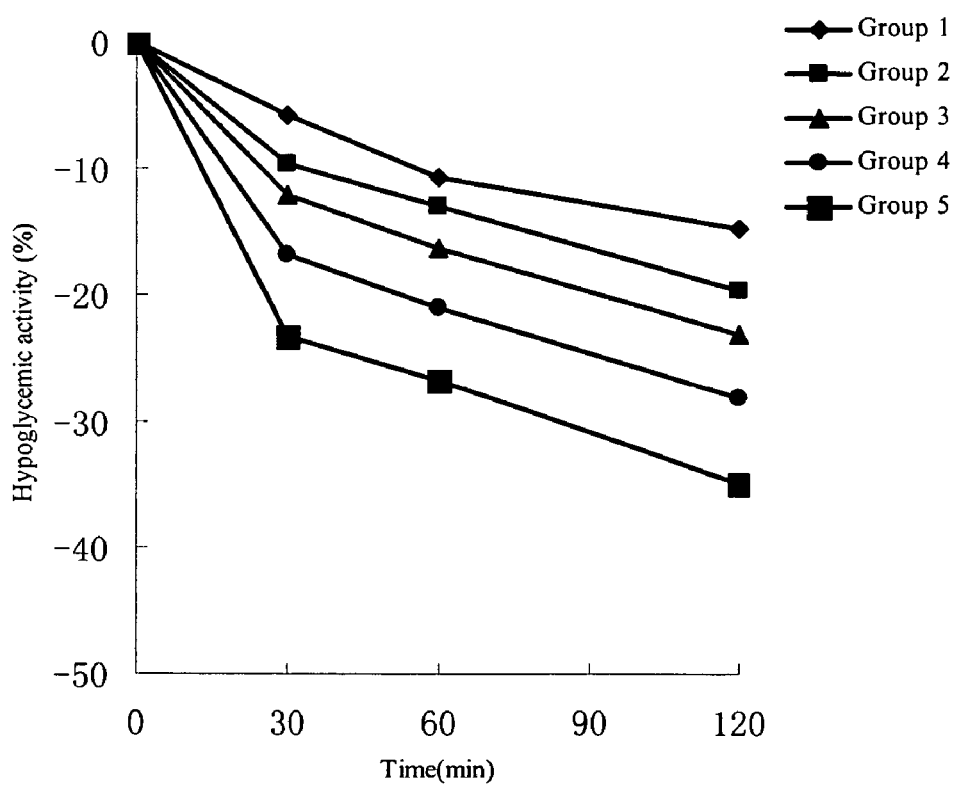
FIG. 20. The hypoglycemic activity of Exendin 4 polypeptide fragment having the sequence of SEQ ID NO. 4 on alloxan induced diabetic mice.
Figure 21:
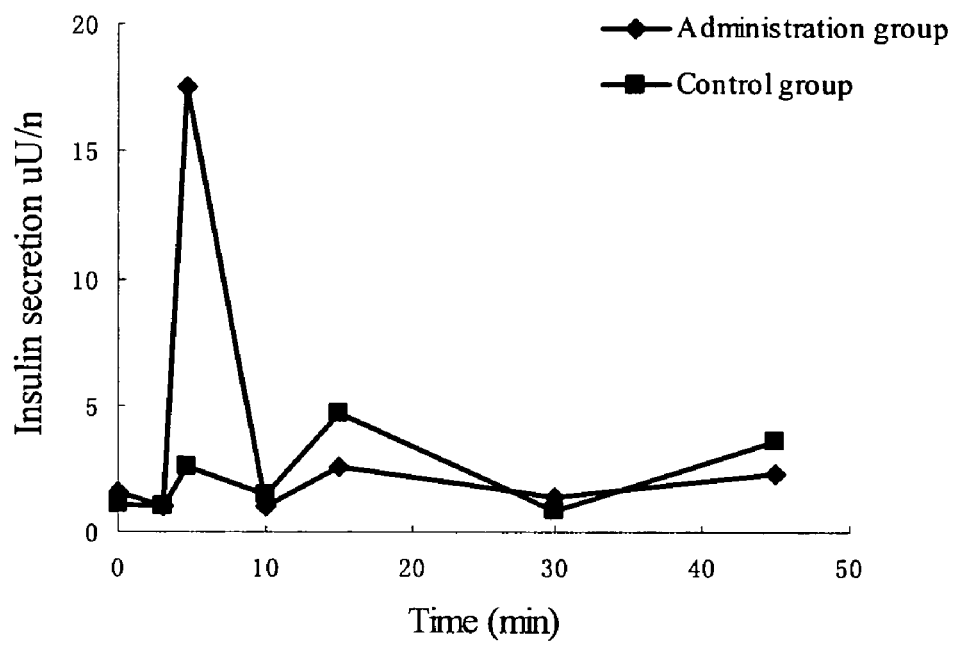
FIG. 21. The insulin secretion stimulated by Exendin 4 polypeptide fragment having the sequence of SEQ ID NO. 4. The curve 1 indicates administration group. The curve 2 indicates blank control group.
Figure 22:
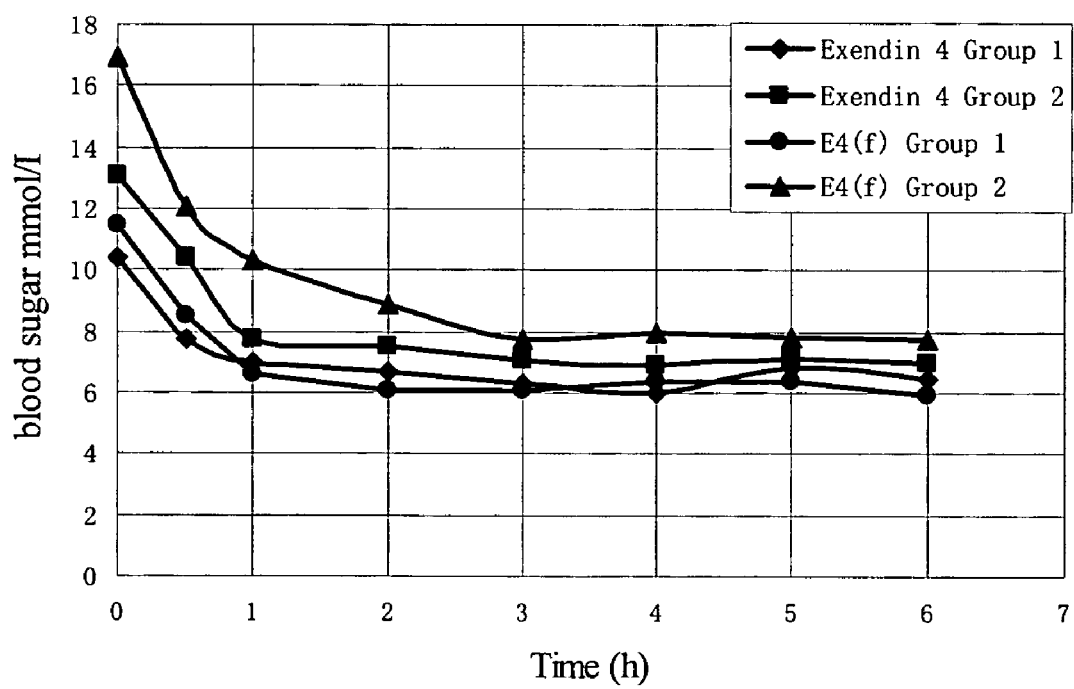
FIG. 22. Comparison of the sustained hypoglycemic activity of Exendin 4 polypeptide fragment having the sequence of SEQ ID NO. 5 with Exendin 4.
Figure 23:
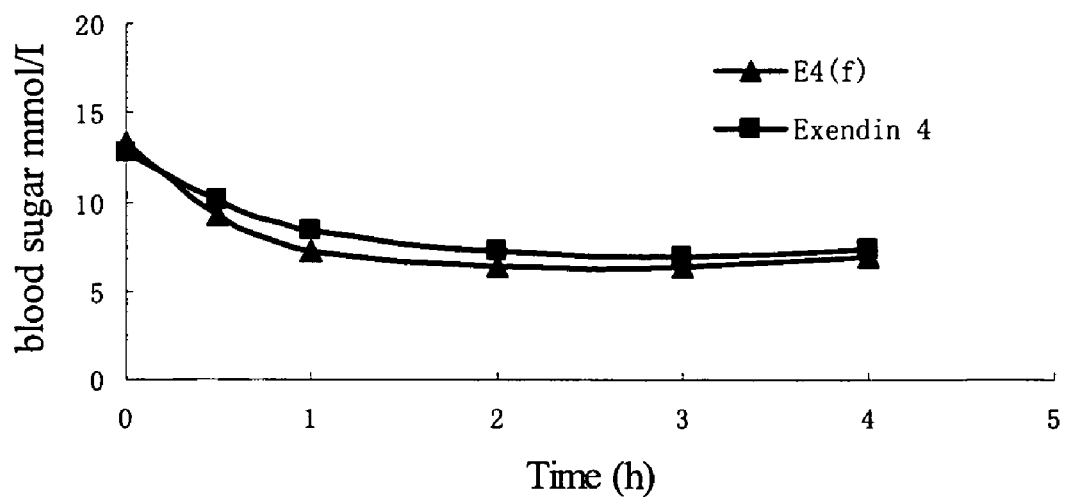
FIG. 23. The hypoglycemic activity of Exendin 4 polypeptide fragment having the sequence of SEQ ID NO. 5 on db/db II diabetic mice.
Figure 24:
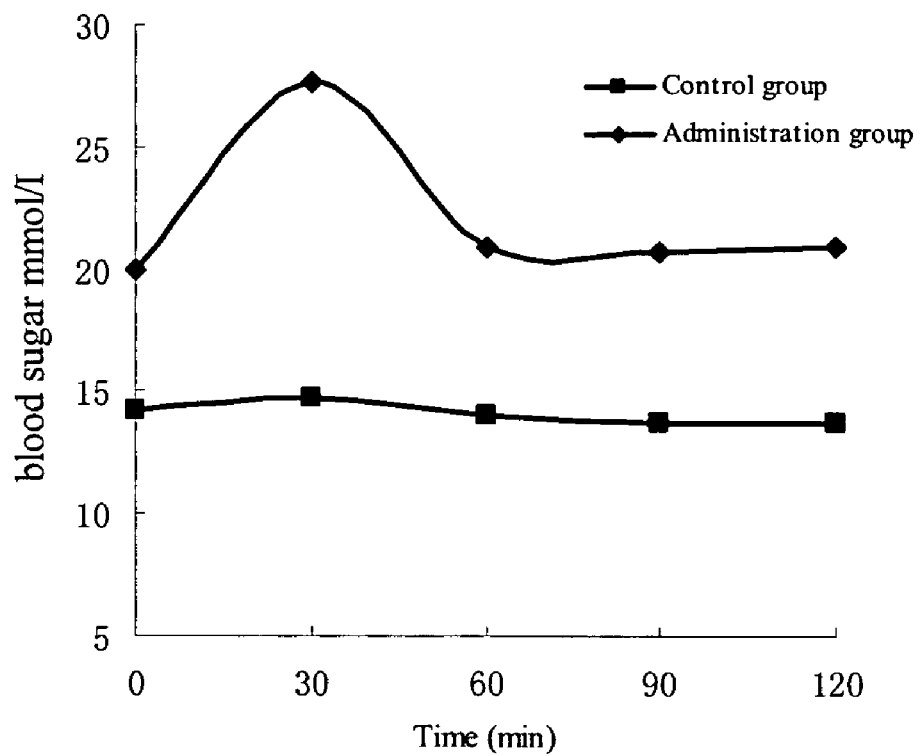
FIG. 24. The postprandial hypoglycemic activity of Exendin 4 polypeptide fragment having the sequence of SEQ ID NO. 5 on Goto-Kokizaki type II diabetic rat. The curve 1 indicates control group. The curve 2 indicates administration group.
Figure 25:
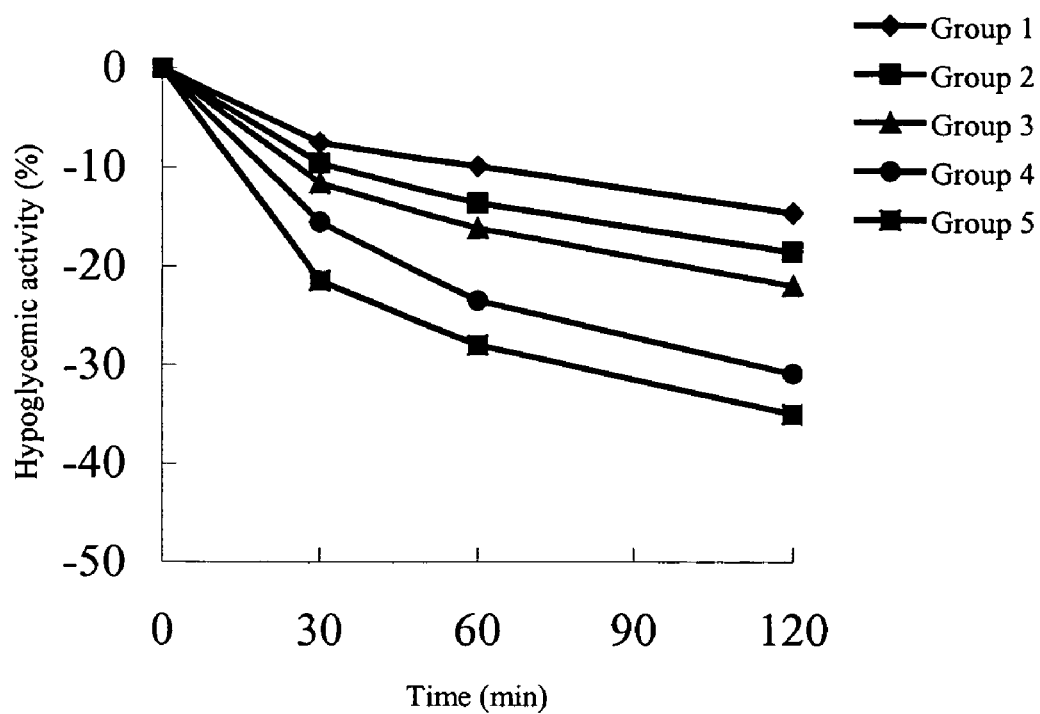
FIG. 25. The hypoglycemic activity of Exendin 4 polypeptide fragment having the sequence of SEQ ID NO. 5 on alloxan induced diabetic mice.
Figure 26:
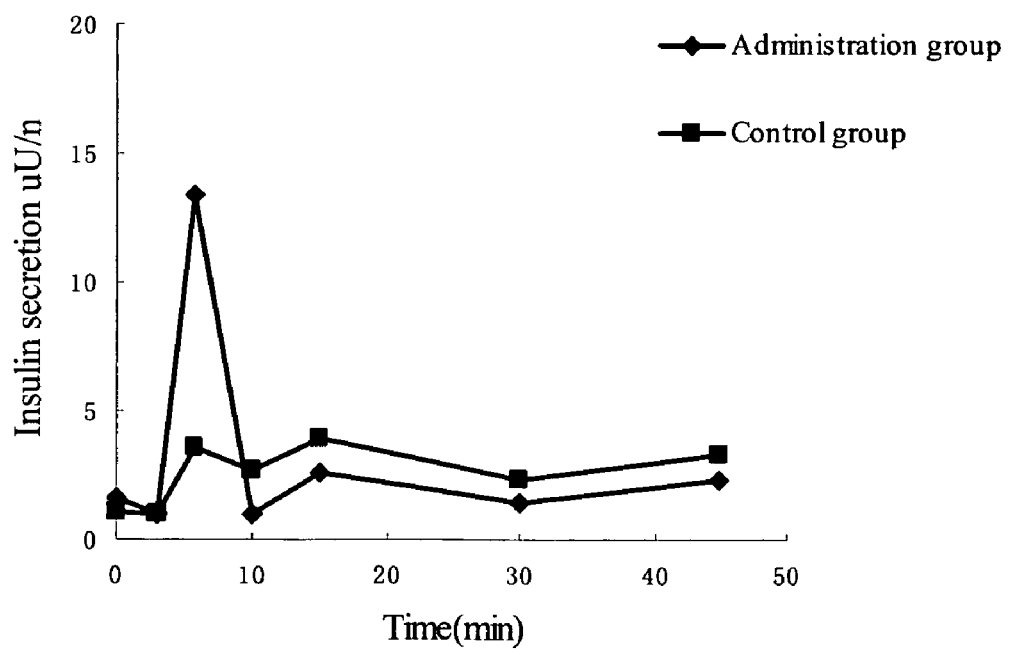
FIG. 26. The insulin secretion stimulated by Exendin 4 polypeptide fragment having the sequence of SEQ ID NO. 5. The curve 1 indicates administration group. The curve 2 indicates blank control group.
Figure 27:
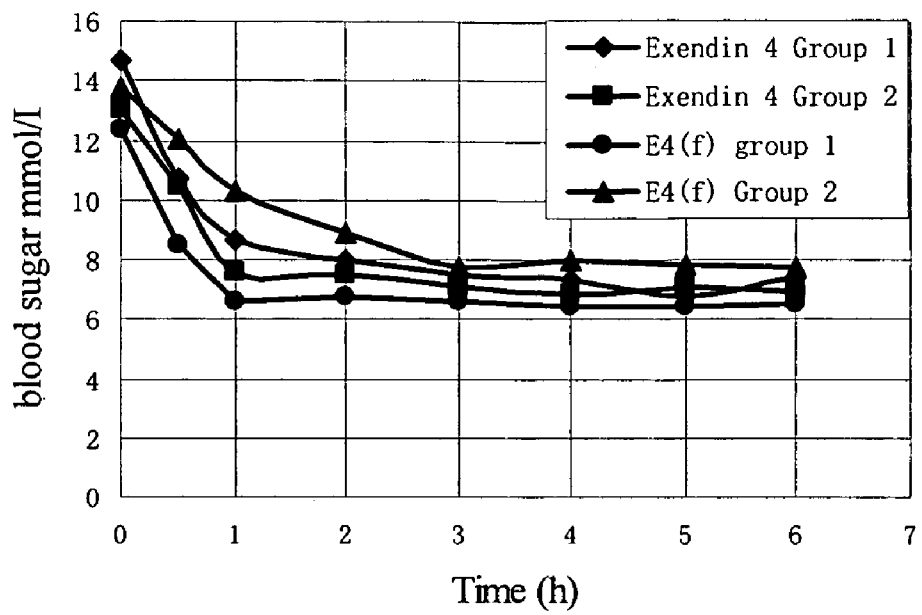
FIG. 27. Comparison of the sustained hypoglycemic activity of Exendin 4 polypeptide fragment having the sequence of SEQ ID NO. 6 with Exendin 4.
Figure 28:
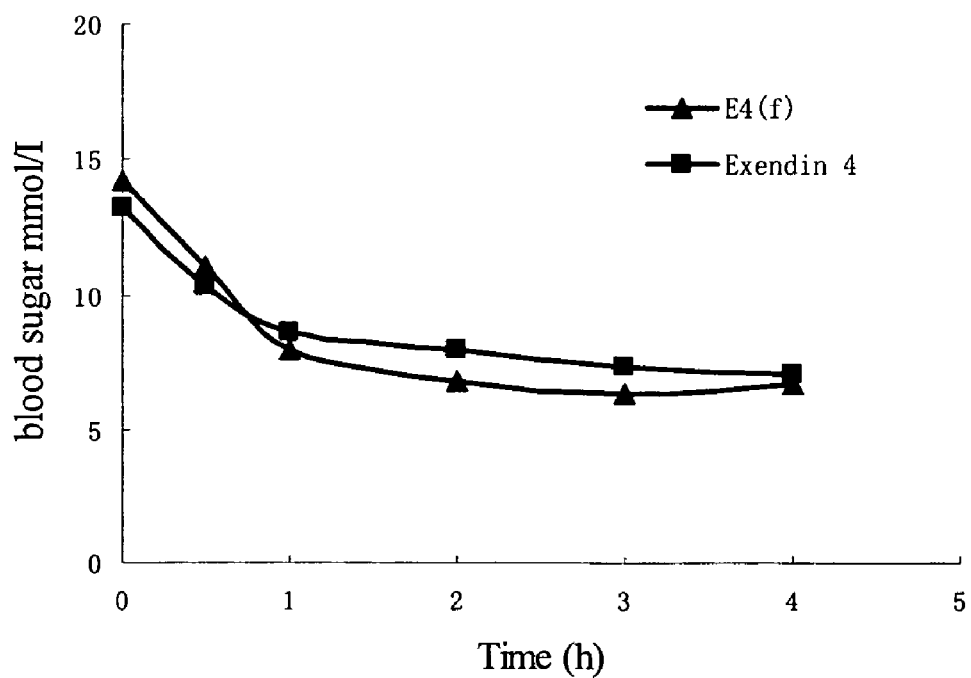
FIG. 28. The hypoglycemic activity of Exendin 4 polypeptide fragment having the sequence of SEQ ID NO. 6 on db/db II diabetic mice.
Figure 29:
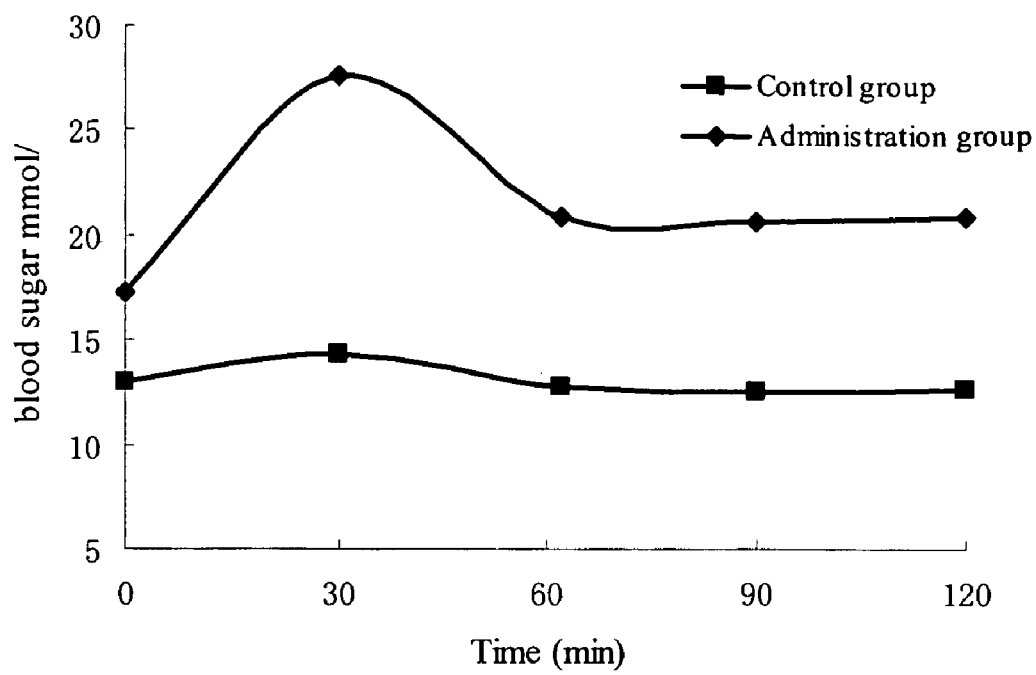
FIG. 29. The postprandial hypoglycemic activity of Exendin 4 polypeptide fragment having the sequence of SEQ ID NO. 6 on Goto-Kokizaki type II diabetic rat. The curve 1 indicates control group. The curve 2 indicates administration group.
Figure 30:
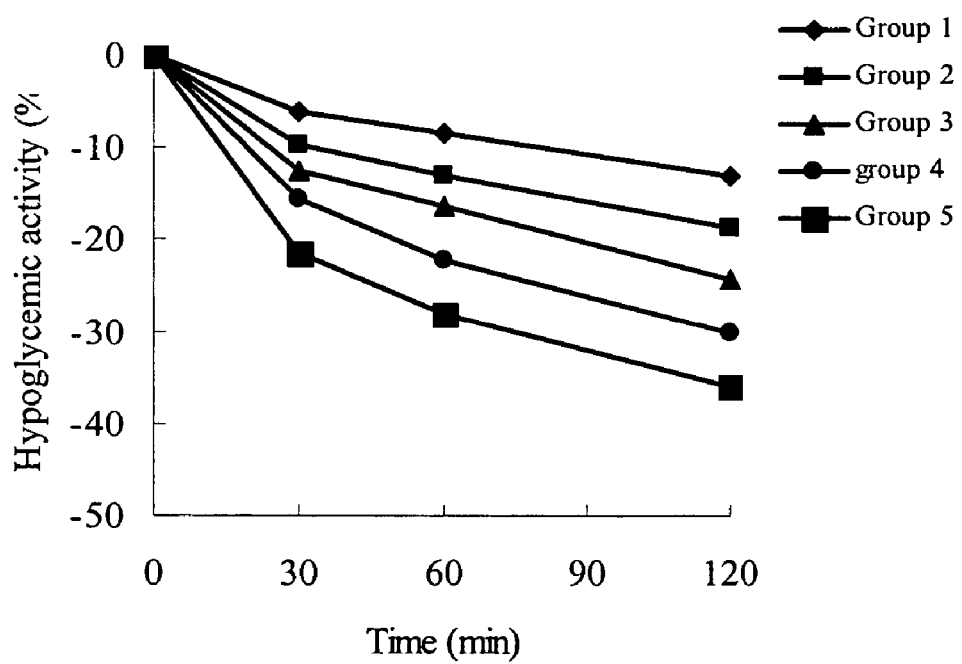
FIG. 30. The hypoglycemic activity of Exendin 4 polypeptide fragment having the sequence of SEQ ID NO. 6 on alloxan induced diabetic mice.
Figure 31:
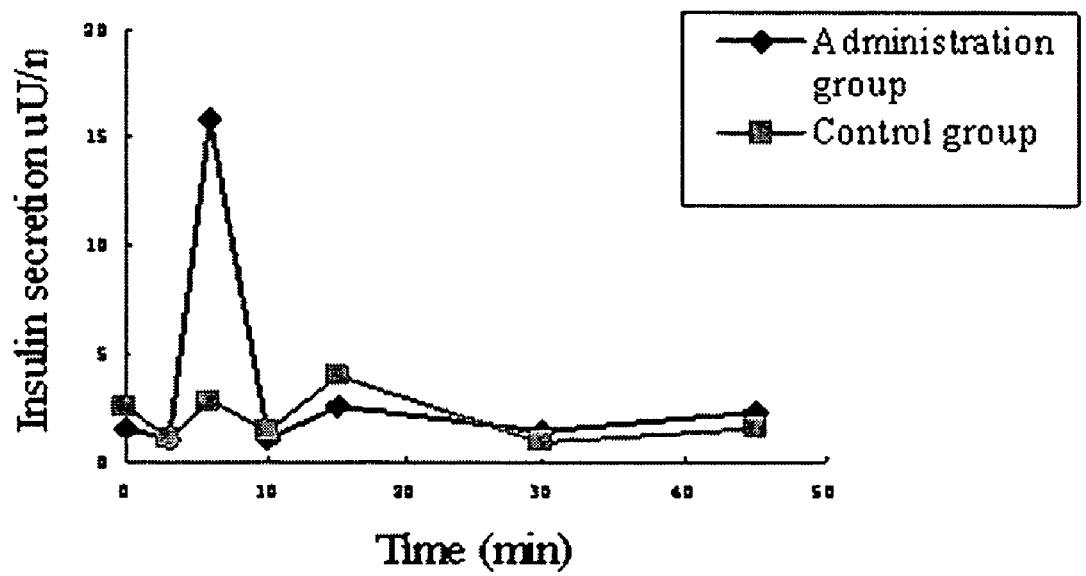
FIG. 31. The insulin secretion stimulated by Exendin 4 polypeptide fragment having the sequence of SEQ ID NO. 6. The curve 1 indicates administration group. The curve 2 indicates blank control group.
Figure 32:
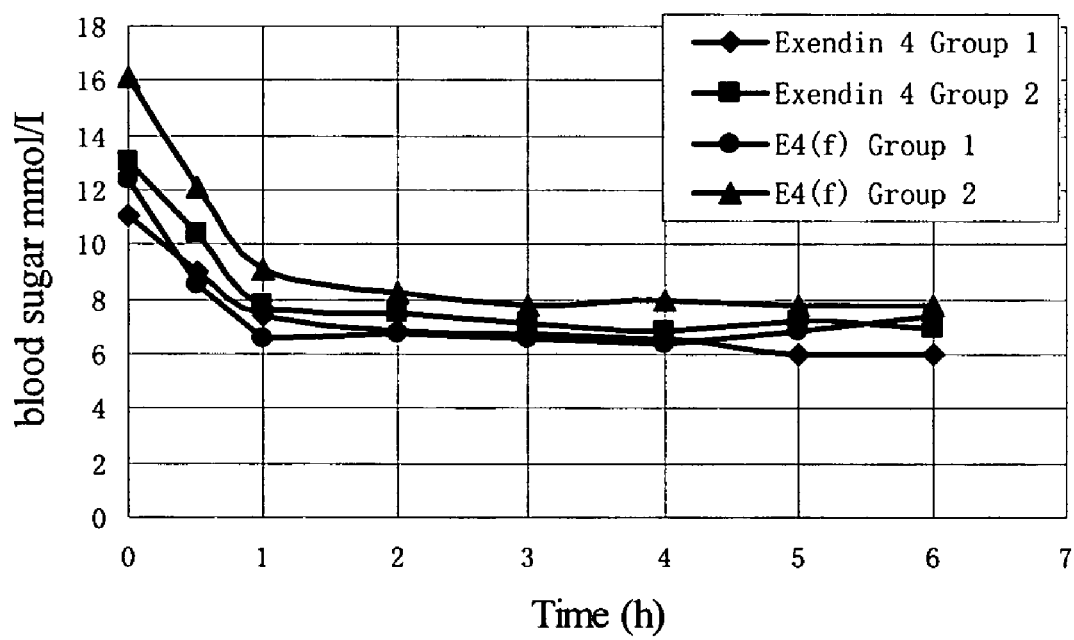
FIG. 32. Comparison of the sustained hypoglycemic activity of Exendin 4 polypeptide fragment having the sequence of SEQ ID NO. 7 with Exendin 4.
Figure 33:
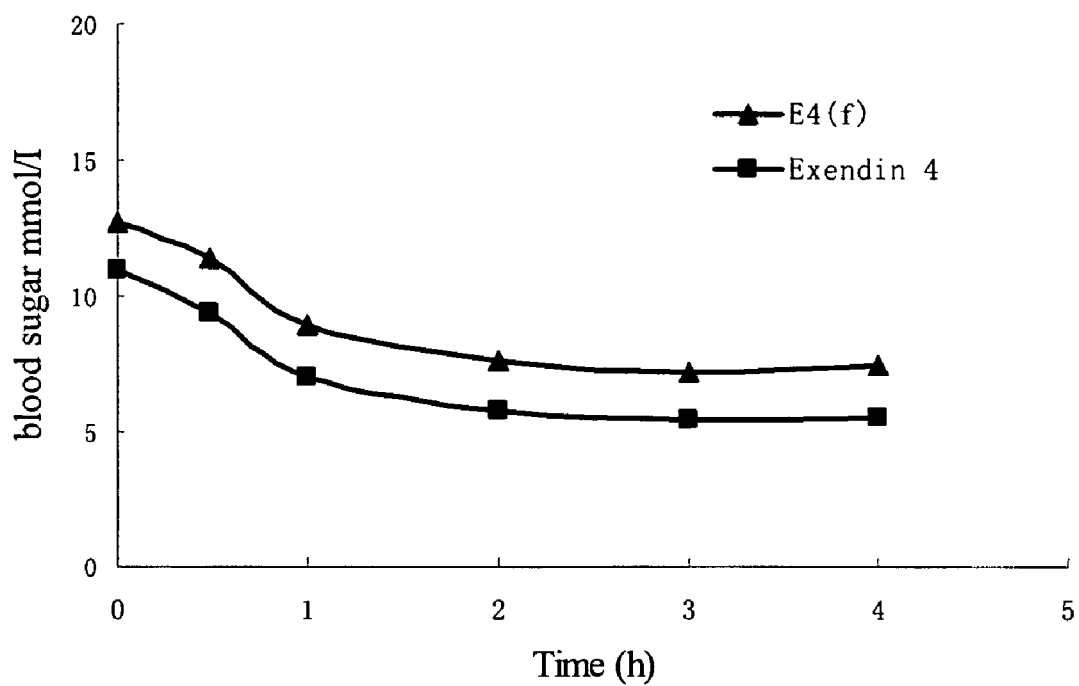
FIG. 33. The hypoglycemic activity of Exendin 4 polypeptide fragment having the sequence of SEQ ID NO. 7 on db/db II diabetic mice.
Figure 34:
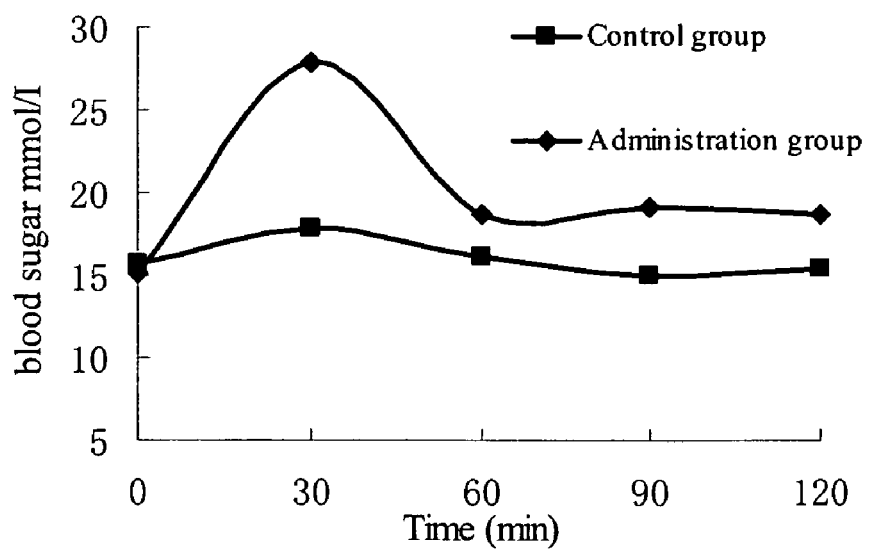
FIG. 34. The postprandial hypoglycemic activity of Exendin 4 polypeptide fragment having the sequence of SEQ ID NO. 7 on Goto-Kokizaki type II diabetic rat. The curve 1 indicates control group. The curve 2 indicates administration group.
Figure 35:
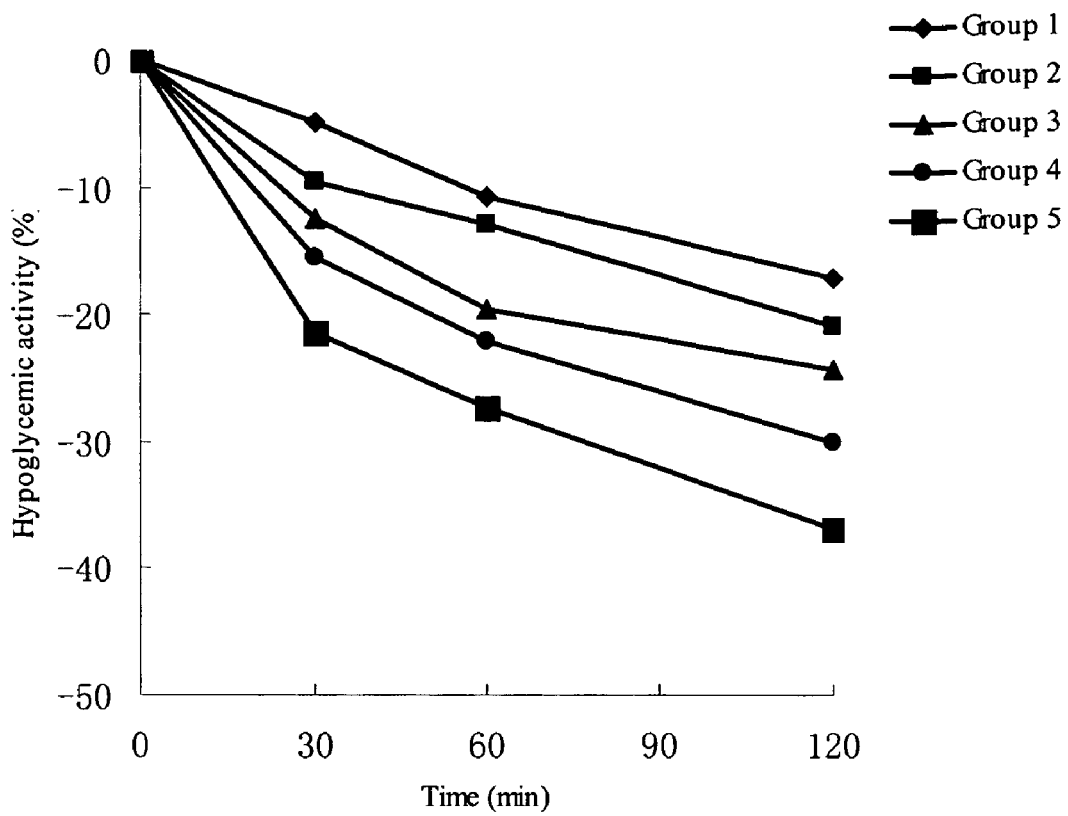
FIG. 35. The hypoglycemic activity of Exendin 4 polypeptide fragment having the sequence of SEQ ID NO. 7 on alloxan induced diabetic mice.
Figure 36:
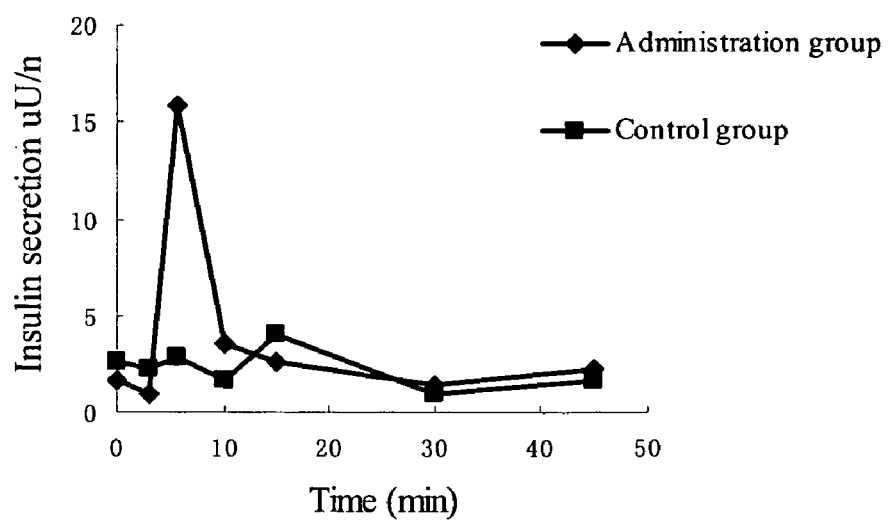
FIG. 36. The insulin secretion stimulated by Exendin 4 polypeptide fragment having the sequence of SEQ ID NO. 7. The curve 1 indicates administration group. The curve 2 indicates blank control group.
Figure 37:
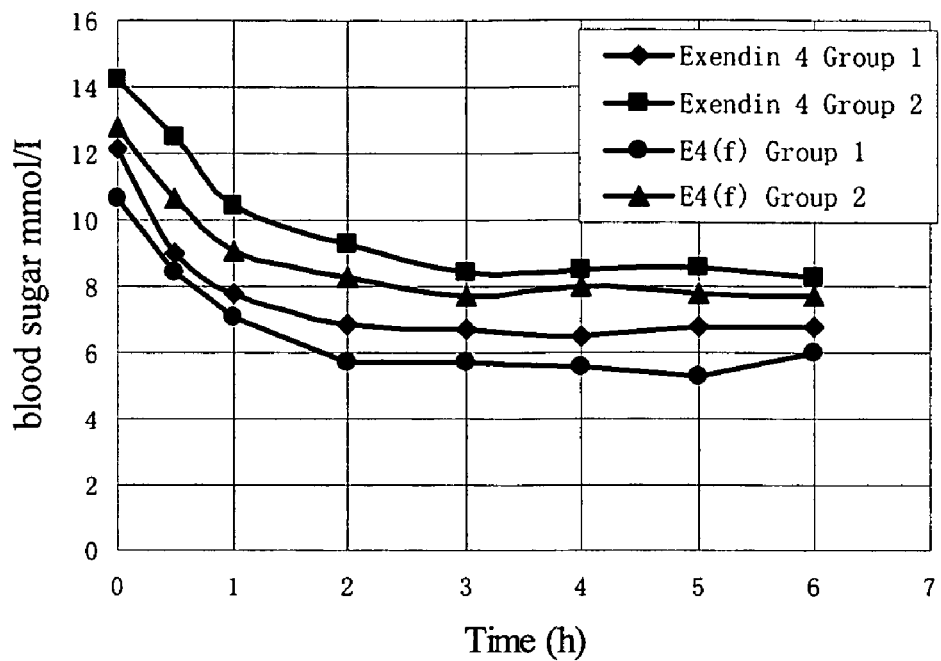
FIG. 37. Comparison of the sustained hypoglycemic activity of Exendin 4 polypeptide fragment having the sequence of SEQ ID NO. 8 with Exendin 4.
Figure 38:
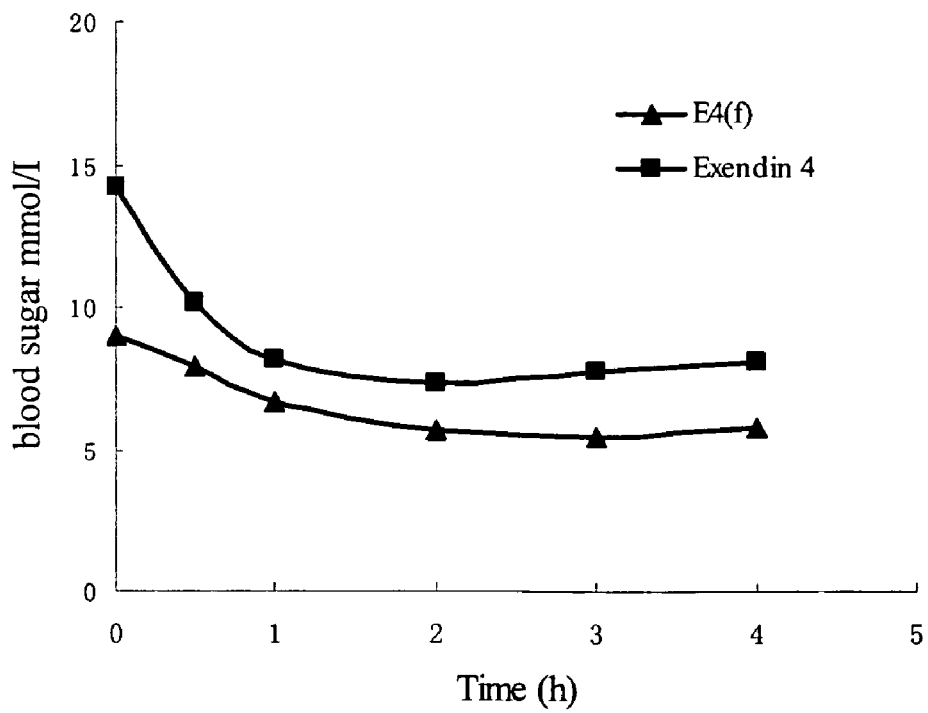
FIG. 38. The hypoglycemic activity of Exendin 4 polypeptide fragment having the sequence of SEQ ID NO. 8 on db/db II diabetic mice.
Figure 39:
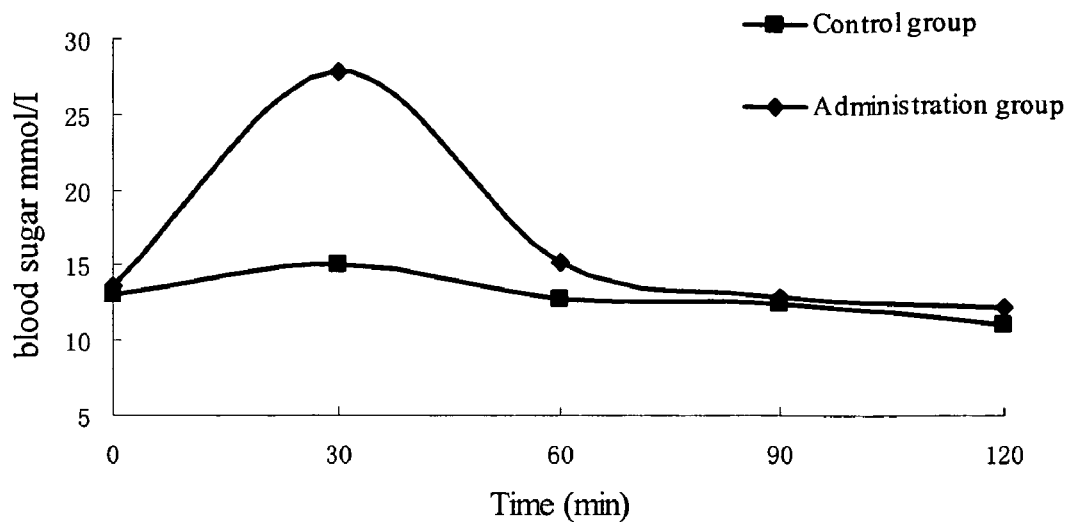
FIG. 39. The postprandial hypoglycemic activity of Exendin 4 polypeptide fragment having the sequence of SEQ ID NO. 8 on Goto-Kokizaki type II diabetic rat. The curve 1 indicates control group. The curve 2 indicates administration group.
Figure 40:
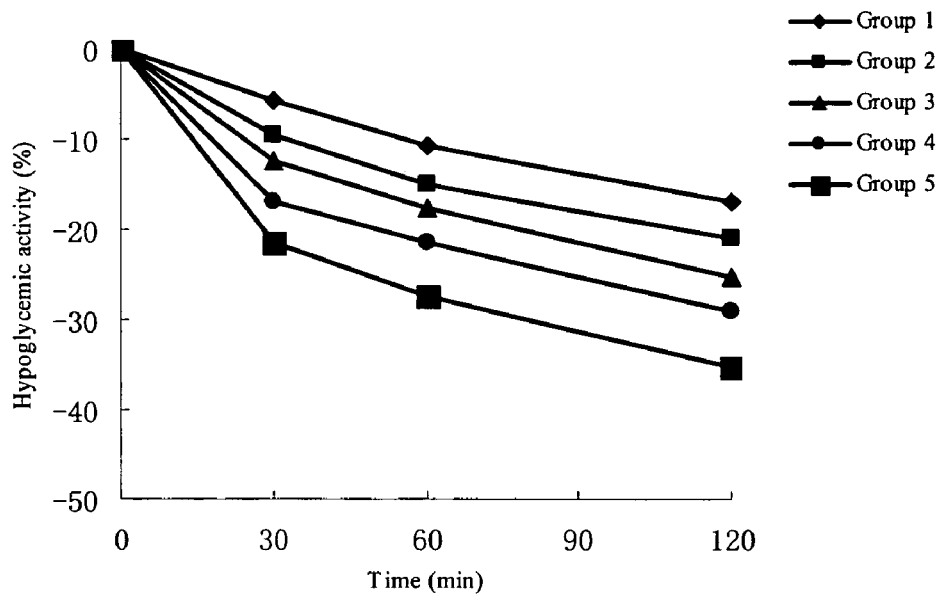
FIG. 40. The hypoglycemic activity of Exendin 4 polypeptide fragment having the sequence of SEQ ID NO. 8 on alloxan induced diabetic mice.
Figure 41:
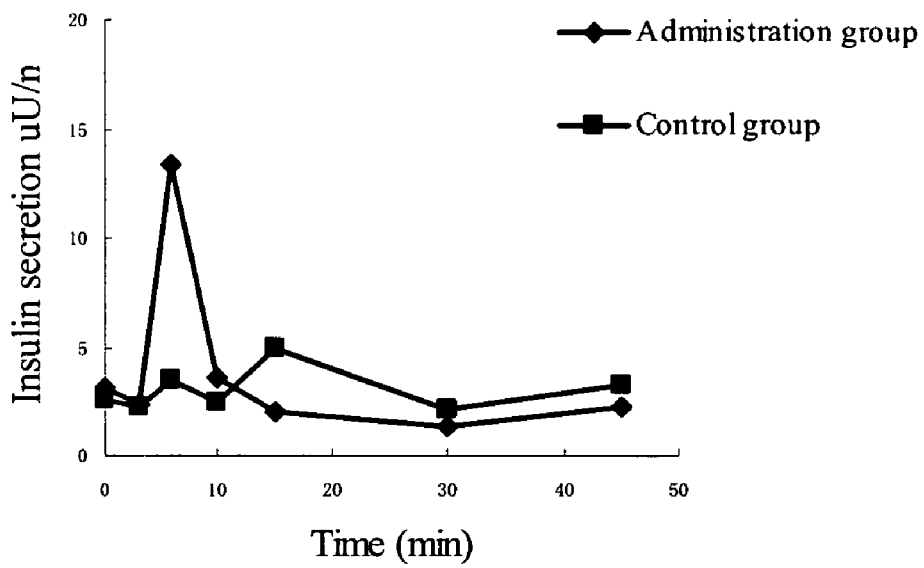
FIG. 41. The insulin secretion stimulated by Exendin 4 polypeptide fragment having the sequence of SEQ ID NO. 8. The curve 1 indicates administration group. The curve 2 indicates blank control group.
Figure 42:
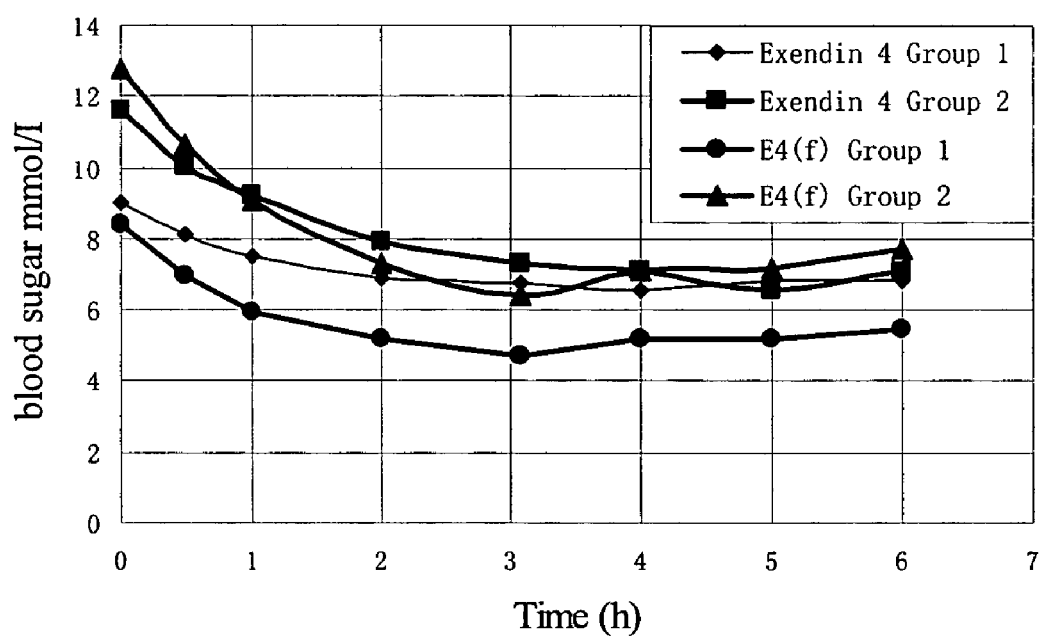
FIG. 42. Comparison of the sustained hypoglycemic activity of Exendin 4 polypeptide fragment having the sequence of SEQ ID NO. 9 with Exendin 4.
Figure 43:
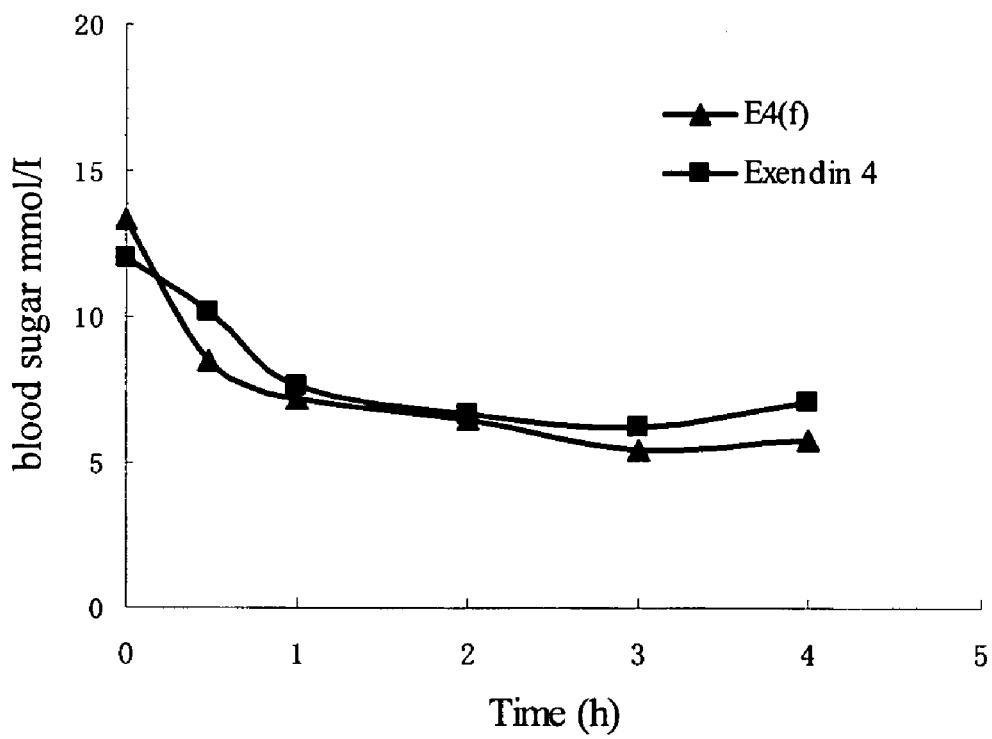
FIG. 43. The hypoglycemic activity of Exendin 4 polypeptide fragment having the sequence of SEQ ID NO. 9 on db/db II diabetic mice.
Figure 44:
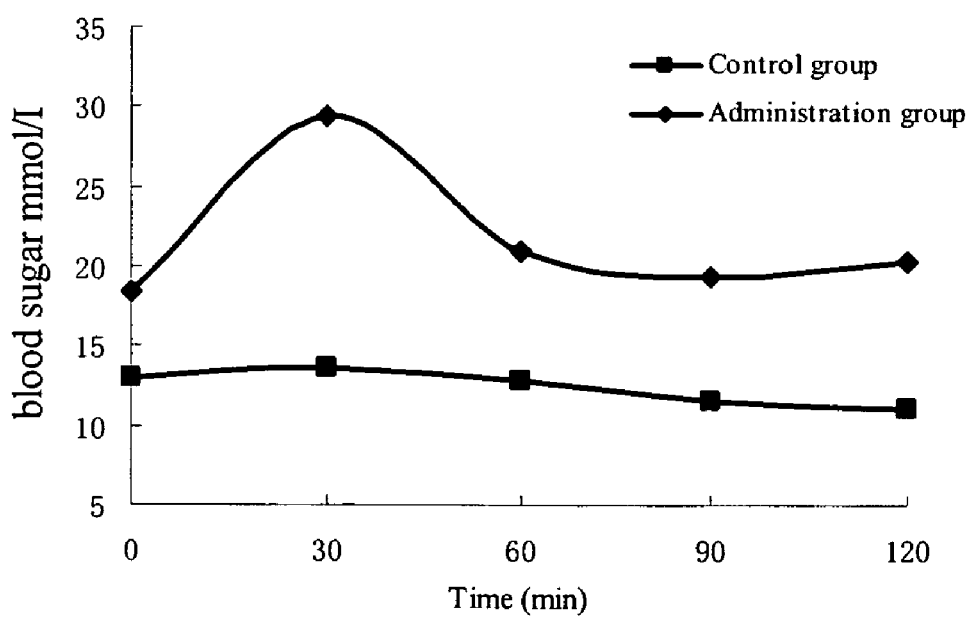
FIG. 44. The postprandial hypoglycemic activity of Exendin 4 polypeptide fragment having the sequence of SEQ ID NO. 9 on Goto-Kokizaki type II diabetic rat. The curve 1 indicates control group. The curve 2 indicates administration group.
Figure 45:
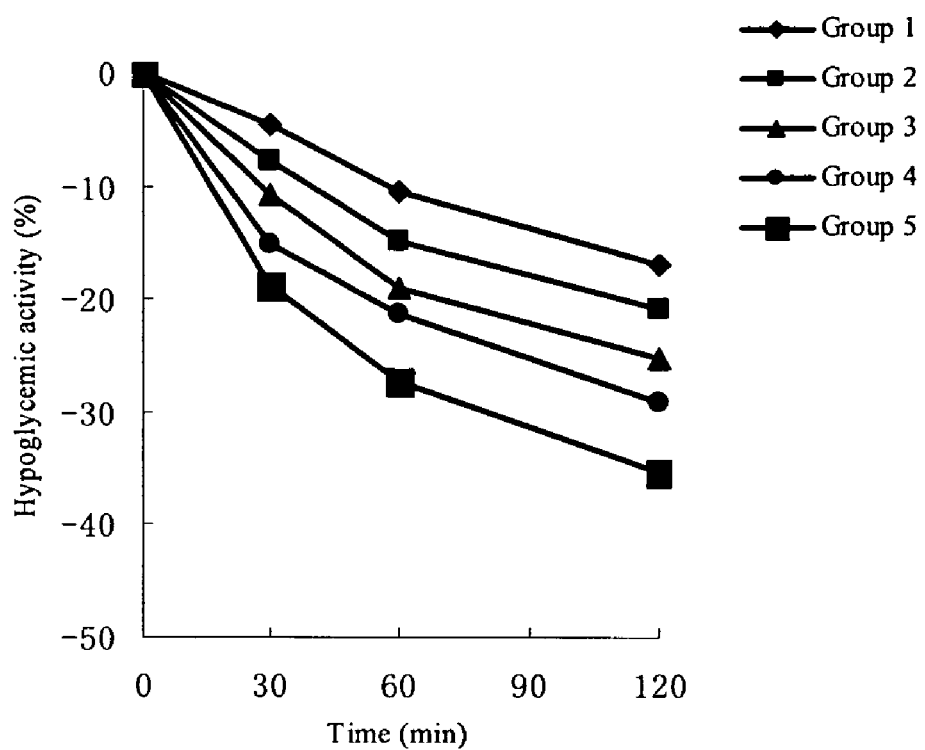
FIG. 45. The hypoglycemic activity of Exendin 4 polypeptide fragment having the sequence of SEQ ID NO. 9 on alloxan induced diabetic mice.
Figure 46:
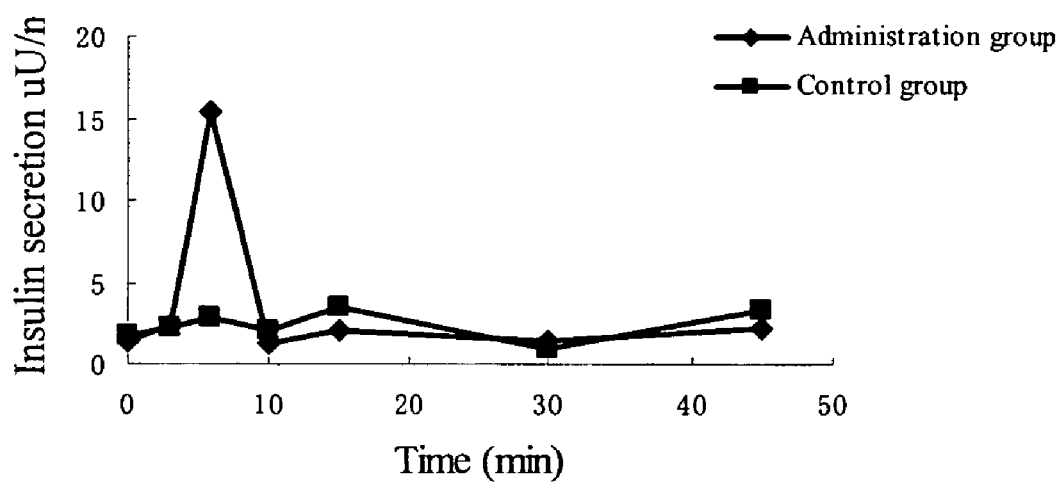
FIG. 46. The insulin secretion stimulated by Exendin 4 polypeptide fragment having the sequence of SEQ ID NO. 9. The curve 1 indicates administration group. The curve 2 indicates blank control group.
Figure 47:
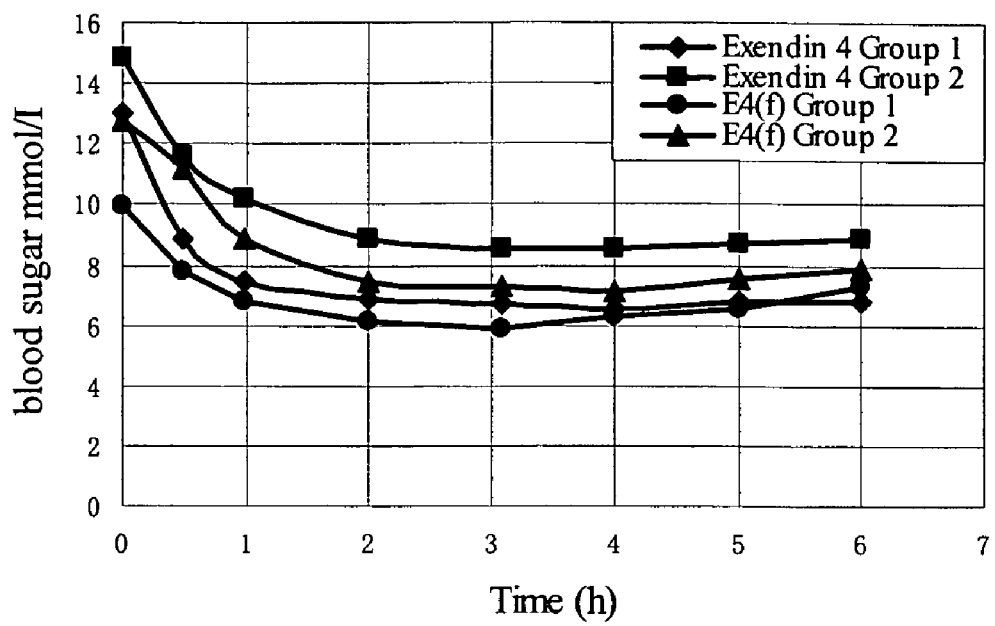
FIG. 47. Comparison of the sustained hypoglycemic activity of Exendin 4 polypeptide fragment having the sequence of SEQ ID NO. 10 with Exendin 4.
Figure 48:
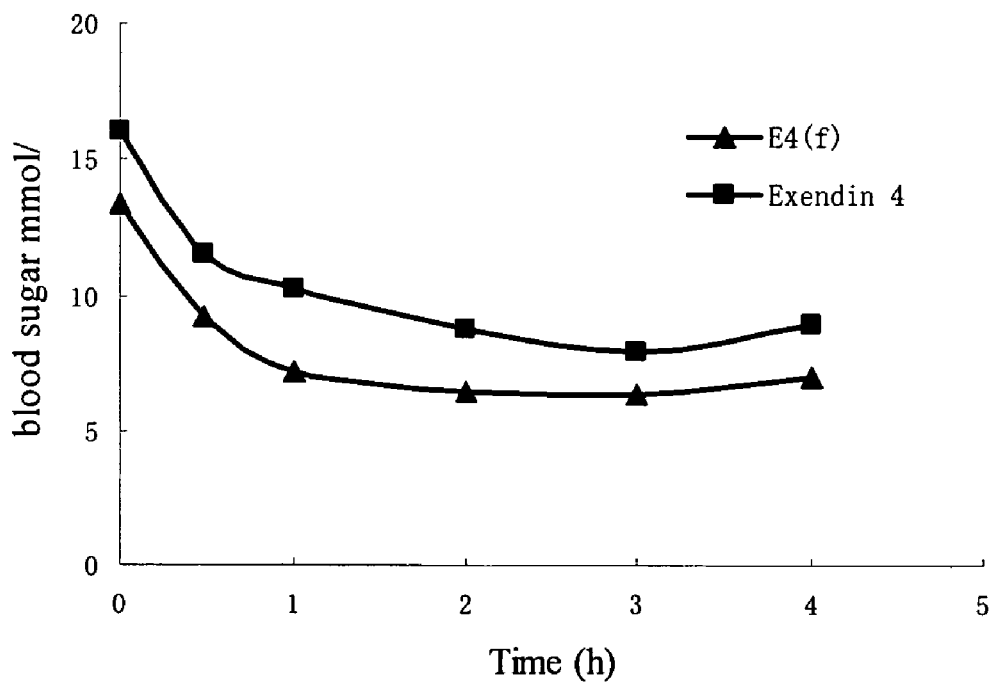
FIG. 48. The hypoglycemic activity of Exendin 4 polypeptide fragment having the sequence of SEQ ID NO. 10 on db/db II diabetic mice.
Figure 49:
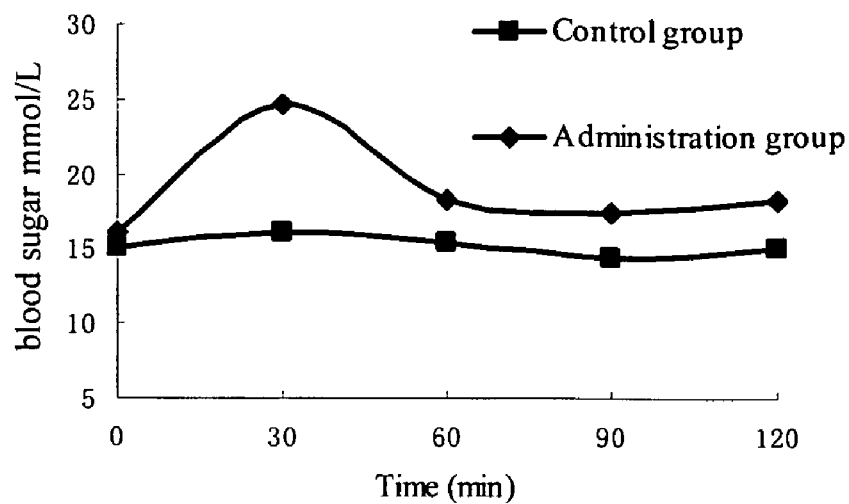
FIG. 49. The postprandial hypoglycemic activity of Exendin 4 polypeptide fragment having the sequence of SEQ ID NO. 10 on Goto-Kokizaki type II diabetic rat. The curve 1 indicates control group. The curve 2 indicates administration group.
Figure 50:
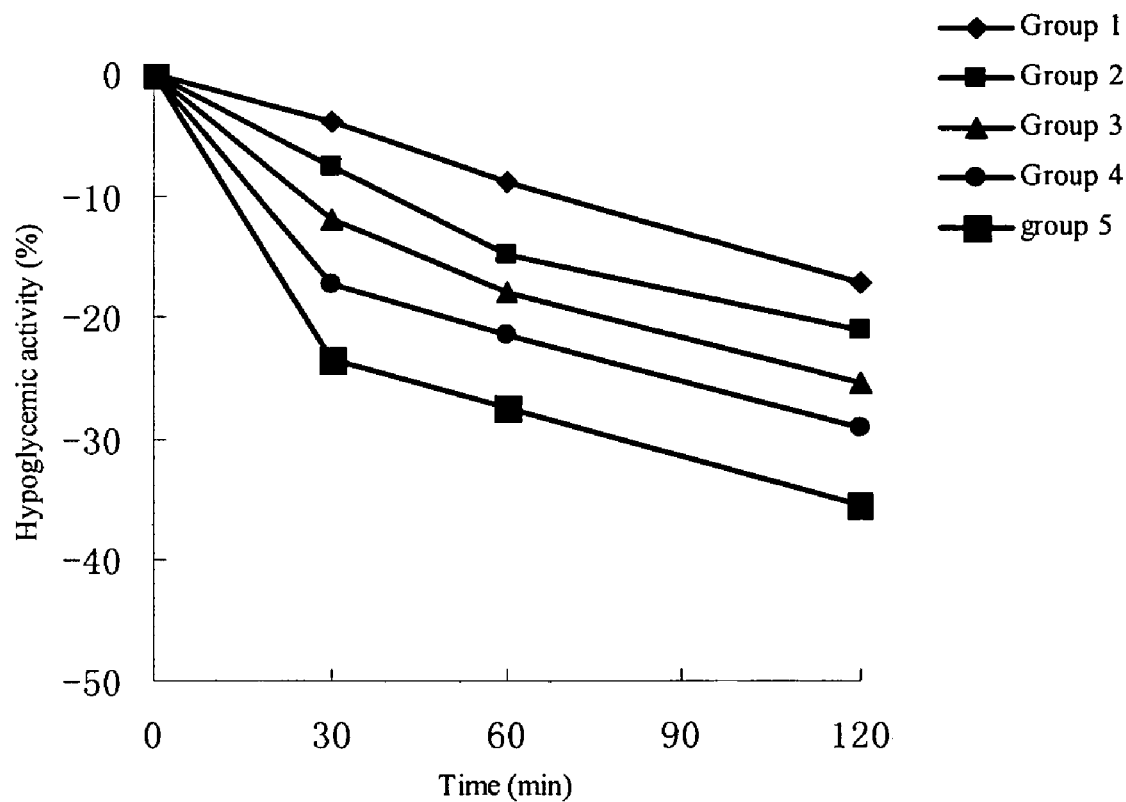
FIG. 50. The hypoglycemic activity of Exendin 4 polypeptide fragment having the sequence of SEQ ID NO. 10 on alloxan induced diabetic mice.
Figure 51:
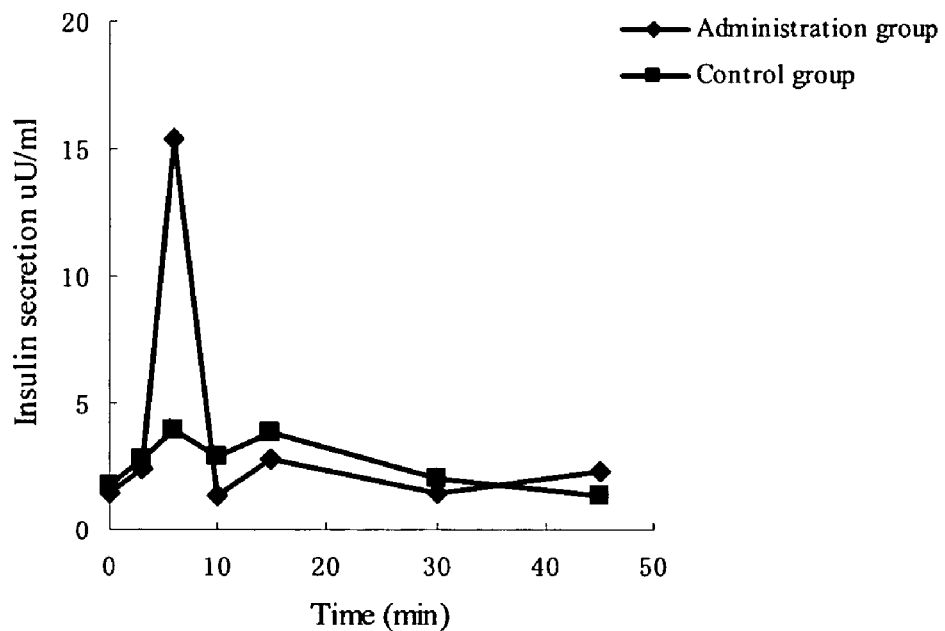
FIG. 51. The insulin secretion stimulated by Exendin 4 polypeptide fragment having the sequence of SEQ ID NO. 10. The curve 1 indicates administration group. The curve 2 indicates blank control group.
Figure 52:
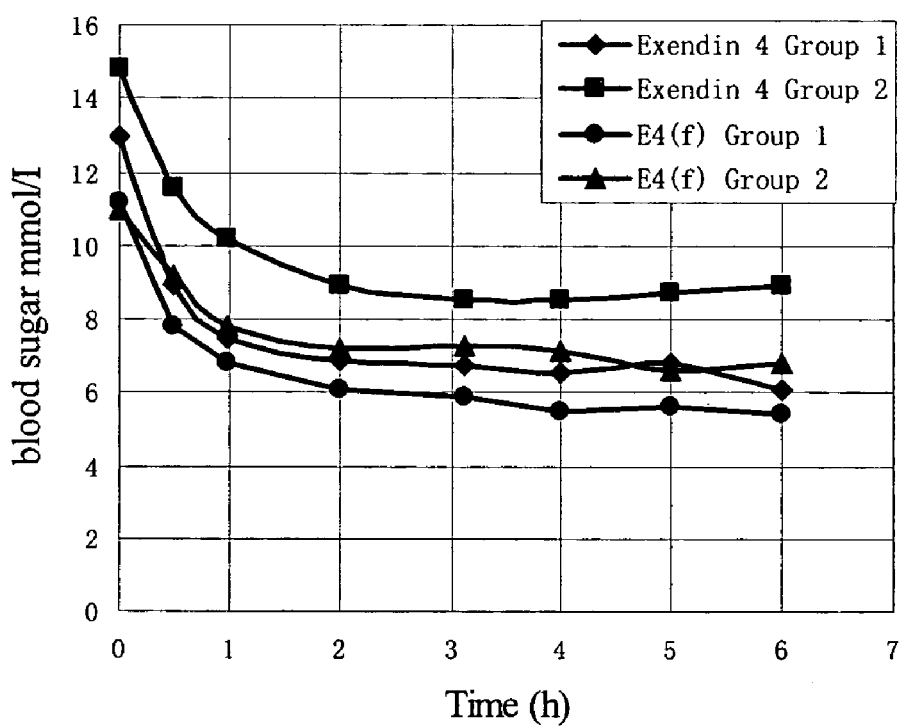
FIG. 52. Comparison of the sustained hypoglycemic activity of Exendin 4 polypeptide fragment having the sequence of SEQ ID NO. 11 with Exendin 4.
Figure 53:
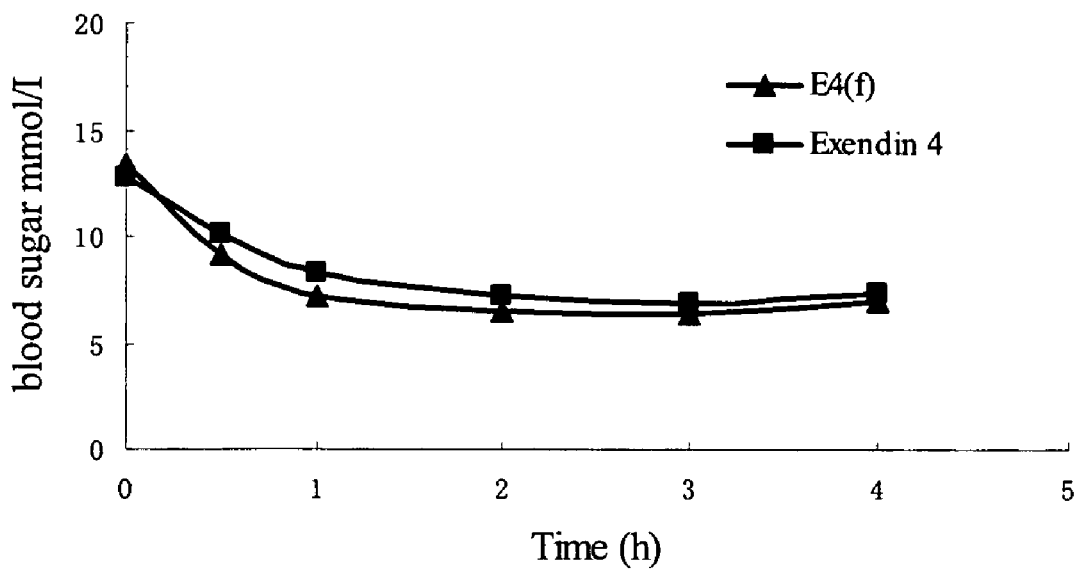
FIG. 53. The hypoglycemic activity of Exendin 4 polypeptide fragment having the sequence of SEQ ID NO. 11 on db/db II diabetic mice.
Figure 54:
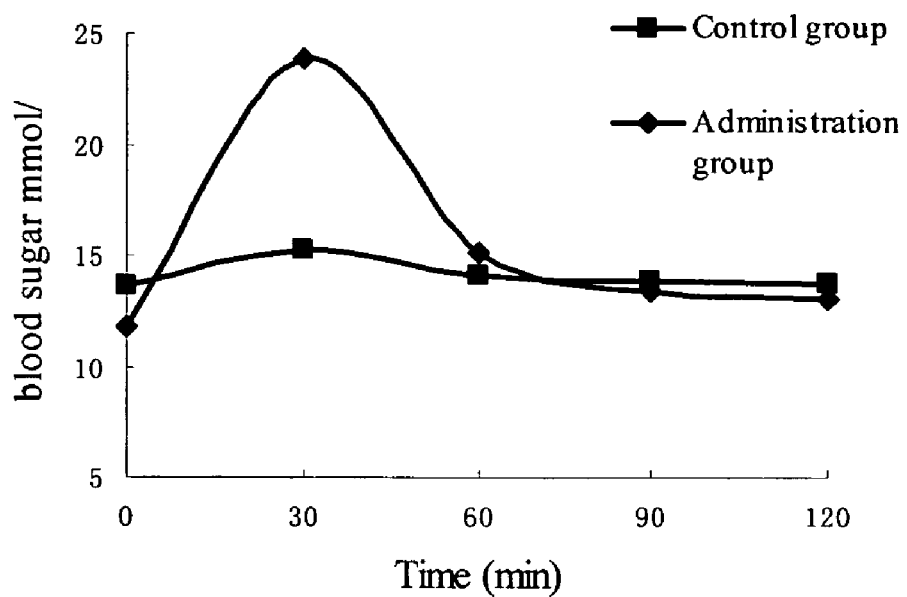
FIG. 54. The postprandial hypoglycemic activity of Exendin 4 polypeptide fragment having the sequence of SEQ ID NO. 11 on Goto-Kokizaki type II diabetic rat. The curve 1 indicates control group. The curve 2 indicates administration group.
Figure 55:
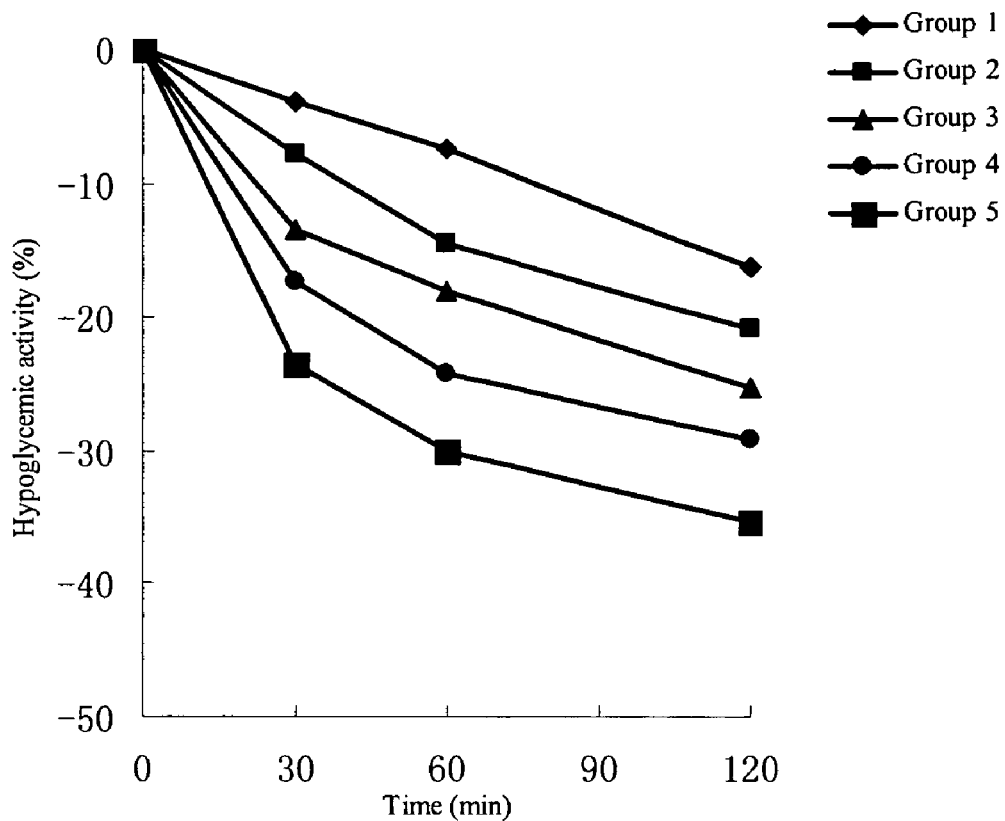
FIG. 55. The hypoglycemic activity of Exendin 4 polypeptide fragment having the sequence of SEQ ID NO. 11 on alloxan induced diabetic mice.
Figure 56:
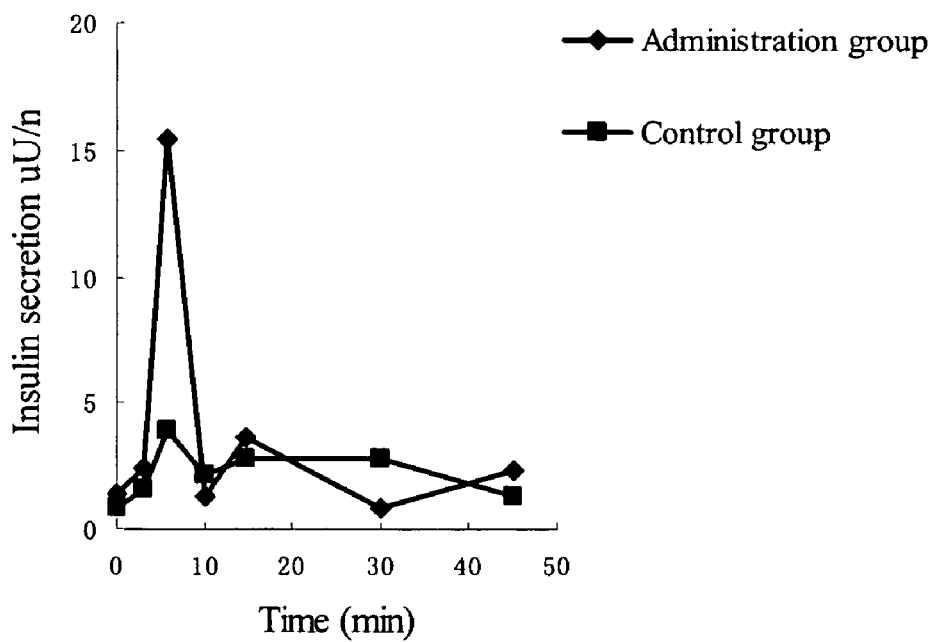
FIG. 56. The insulin secretion stimulated by Exendin 4 polypeptide fragment having the sequence of SEQ ID NO. 11. The curve 1 indicates administration group. The curve 2 indicates blank control group.
Figure 57:
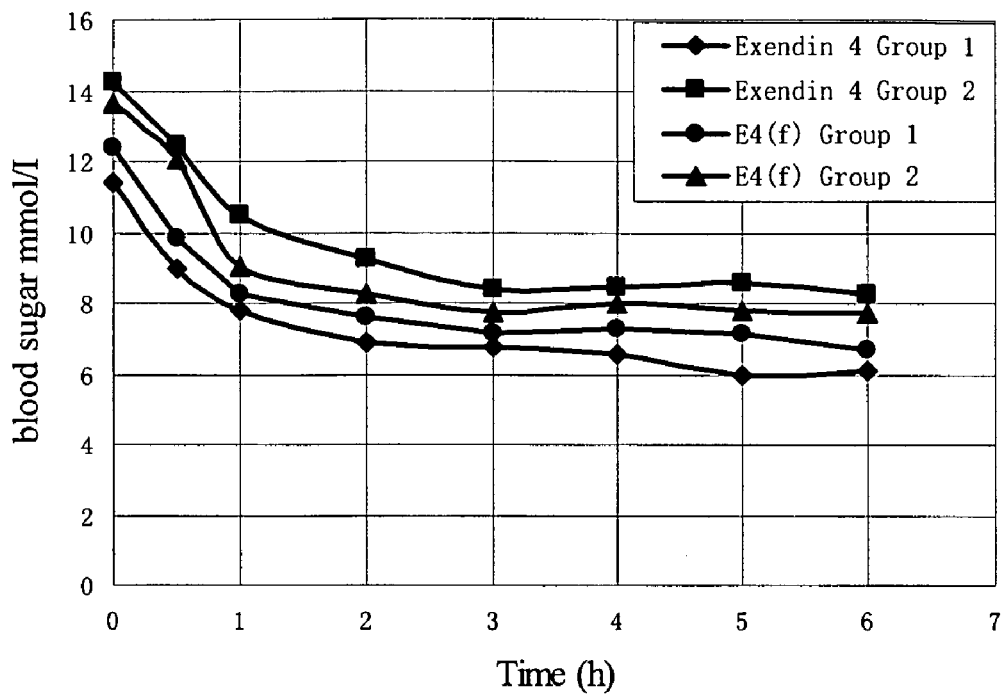
FIG. 57. Comparison of the sustained hypoglycemic activity of Exendin 4 polypeptide fragment having the sequence of SEQ ID NO. 12 with Exendin 4.
Figure 58:
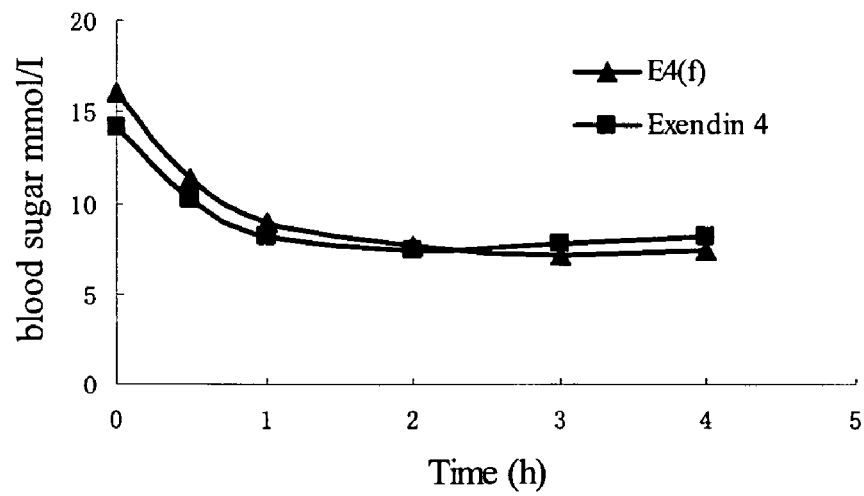
FIG. 58. The hypoglycemic activity of Exendin 4 polypeptide fragment having the sequence of SEQ ID NO. 12 on db/db II diabetic mice.
Figure 59:
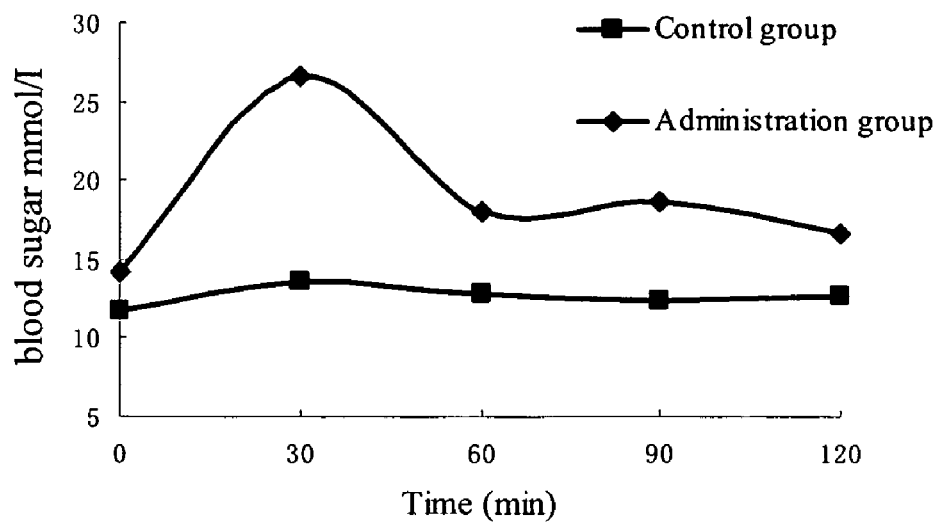
FIG. 59. The postprandial hypoglycemic activity of Exendin 4 polypeptide fragment having the sequence of SEQ ID NO. 12 on Goto-Kokizaki type II diabetic rat. The curve 1 indicates control group. The curve 2 indicates administration group.
Figure 60:
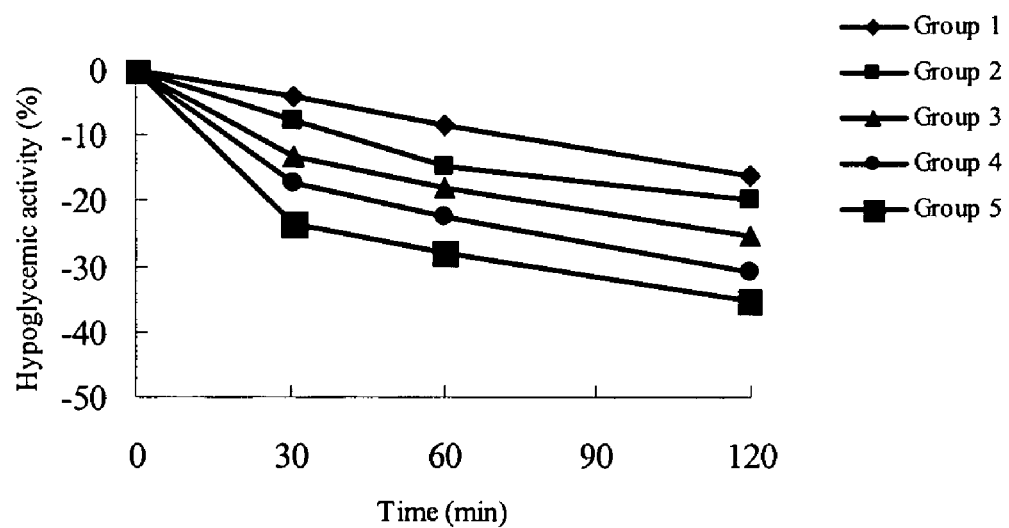
FIG. 60. The hypoglycemic activity of Exendin 4 polypeptide fragment having the sequence of SEQ ID NO. 12 on alloxan induced diabetic mice.
Figure 61:
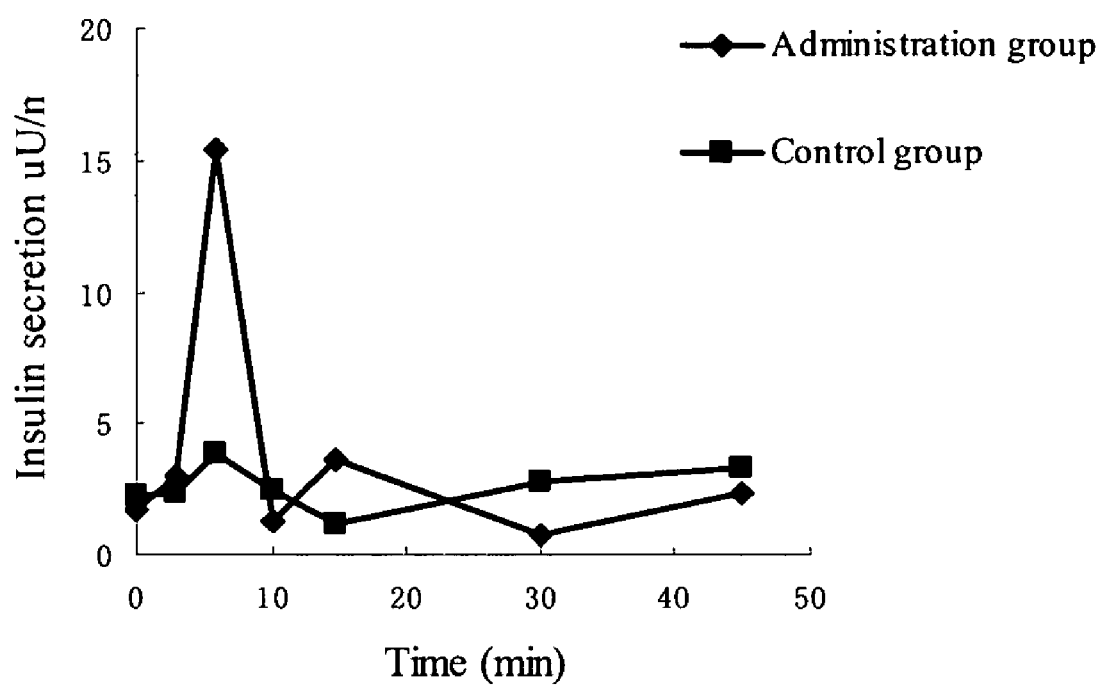
FIG. 61. The insulin secretion stimulated by Exendin 4 polypeptide fragment having the sequence of SEQ ID NO. 12. The curve 1 indicates administration group. The curve 2 indicates blank control group.

Six-month-old (470 g body weight) Goto Kokizaki II rats were taken for the operative procedure. The test animals were administrated by subcutaneous injection of Exendin 4 polypeptides in a dose of 5 µg, while the animals of control group only achieved physiological saline solution. 20 µl of blood samples were obtained from fasted animals at 0, 3, 5, 10, 15, 30 and 45 minutes time points respectively after administration of the test substance. The insulin secretion stimulated by Exendin 4 polypeptide fragment is determined by using ELISA kit (Dianostic Systemlab Inc., USA. The results are shown in FIG. 6. The animals of test group recovered the first-phase insulin secretion, which were administrated by subcutaneous injection of Exendin 4 polypeptide having the sequence of SEQ ID NO. 2.

The corresponding results of the Exendin 4 polypeptide fragments having the sequences of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11 and SEQ ID NO. 12 are shown in FIG. 11, FIG. 6, FIG. 16, FIG. 21, FIG. 26, FIG. 31, FIG. 36, FIG. 41, FIG. 46, FIG. 51, FIG. 56, FIG. 61 respectively.

Example 8

The solid phase Exendin 4 polypeptide variants having the sequences of SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71 and SEQ ID NO. 72 were respectively prepared according to the same method as mentioned in example 1.

According to the method as mentioned in examples 3, 4, 5, 6, 7, the sustained hypoglycemic activity assay, the hypoglycemic activity assay on db/db II diabetic mice, the postprandial hypoglycemic activity assay on Goto-Kokizaki type II diabetic rat, the hypoglycemic activity assay on alloxan induced diabetic mice and the insulin secretion stimulation assay were carried out using the Exendin 4 polypeptide fragments (SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71 and SEQ ID NO. 72). The significant hypoglycemic activity was observed with all of the above mentioned polypeptide fragments.

The blood sugar of the KK type II diabetic mice, db/db II diabetic mice and alloxan induced diabetic mice using the Exendin 4 polypeptide fragments (SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71 and SEQ ID NO. 72) were sustainedly reduced 35%~50% within 6 hours, 50%~60% within 4 hours and 30%~40% within 2 hours respectively. The fasted blood sugar of the Goto-Kokizaki type II diabetic rat using the Exendin4 polypeptide fragments (SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71 and SEQ ID NO. 72) was reduced 10% to 20% sustainedly within two hours. The insulin secretion of the test groups which were administrated by injection of Exendin 4 polypeptides fragments (SEQ ID NO. 61, SEQ ID NO. 62, SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71 and SEQ ID NO. 72) was recovered.

We claim:

1. A polypeptide, pharmaceutically acceptable salt, or ester thereof, comprising the sequence represented by SEQ ID 73.

2. The polypeptide of claim 1 comprising the sequence represented by SEQ ID 74.

3. The polypeptide of claim 1 comprising the sequence represented by SEQ ID 75.

4. The polypeptide of claim 1 comprising the sequence represented by SEQ ID 76.

5. The polypeptide of claim 1, comprising the sequence represented by SEQ ID 4.

6. A pharmaceutical composition containing one or more of polypeptides stated in any one of claims 1-5.

7. The pharmaceutical composition of claim 6, further containing pharmaceutically acceptable thinners, excipients or carriers.

8. The pharmaceutical composition of claim 7, wherein the carriers described refer to one or more of ethanol, glycerol, or water.

9. A method for treating diabetes mellitus, the method comprising administering one or several kinds of polypeptides stated in any one of claims 1-5.

10. The method of claim 9, wherein diabetes mellitus is type II diabetes mellitus.

* * * * *